United States Patent [19]
Green et al.

[11] Patent Number: 5,484,095
[45] Date of Patent: Jan. 16, 1996

[54] APPARATUS FOR ENDOSCOPICALLY APPLYING STAPLES INDIVIDUALLY TO BODY TISSUE

[75] Inventors: David T. Green, Westport; Henry Bolanos, East Norwalk; Lisa W. Heaton, Norwalk; Mark E. Alari, Derby; Ghaleb A. Sater, Shelton, all of Conn.

[73] Assignee: United States Surgical Corporation, Norwalk, Conn.

[21] Appl. No.: 144,160

[22] Filed: Oct. 27, 1993

Related U.S. Application Data

[63] Continuation-in-part of Ser. No. 861,065, Mar. 31, 1992, Pat. No. 5,364,002.

[51] Int. Cl.⁶ .................................................. A61B 17/00
[52] U.S. Cl. .................. 227/181.1; 606/139; 606/143; 227/182.1; 227/176.1; 227/175.1
[58] Field of Search .................................. 606/139, 142, 606/143, 151, 205–207; 227/175–182, 901, 19

[56] References Cited

U.S. PATENT DOCUMENTS

| | | |
|---|---|---|
| D. 271,332 | 11/1883 | Green et al. . |
| D. 284,219 | 6/1886 | Green et al. . |
| D. 286,439 | 10/1886 | Green et al. . |
| 3,665,924 | 5/1972 | Noiles et al. . |
| 3,735,762 | 5/1973 | Bryan et al. ............................ 606/143 |
| 4,086,926 | 5/1978 | Green et al. . |
| 4,204,623 | 5/1980 | Green ....................................... 227/19 |
| 4,226,242 | 10/1980 | Jarvik . |
| 4,242,902 | 1/1981 | Green ..................................... 606/143 |
| 4,349,028 | 9/1982 | Green . |
| 4,410,125 | 10/1983 | Noiles et al. . |
| 4,556,058 | 12/1985 | Green . |
| 4,562,839 | 1/1986 | Blake, III et al. ...................... 606/143 |
| 4,569,346 | 2/1986 | Poirier . |
| 4,576,165 | 3/1986 | Green et al. . |
| 4,714,187 | 12/1987 | Green ....................................... 227/19 |
| 4,788,978 | 12/1988 | Strekopytov et al. . |
| 4,821,721 | 4/1989 | Chin et al. . |
| 4,869,414 | 9/1989 | Green et al. ............................. 227/19 |
| 4,892,244 | 1/1990 | Fox et al. . |
| 5,032,127 | 7/1991 | Frazee et al. . |
| 5,035,692 | 7/1991 | Lyon et al. . |
| 5,080,275 | 1/1992 | Heimerl et al. . |
| 5,100,420 | 3/1992 | Green et al. ........................... 606/143 |
| 5,271,543 | 12/1993 | Grant et al. ............................ 227/180 |

*Primary Examiner*—Stephen C. Pellegrino
*Assistant Examiner*—Jeffrey A. Schmidt

[57] ABSTRACT

An apparatus is disclosed for endoscopic application of surgical staples for fastening body tissue, especially vascular tissue. The apparatus includes a frame and an elongated endoscopic section connected to the frame and extending distally therefrom. A staple storage cartridge cooperates with the distal end of the endoscopic section and is selectively pivotal by the user. A staple firing mechanism advances an individual staple against an anvil for staple closure. Means are provided to prevent incomplete staple firing. Relative motion between the staple cartridge and the anvil clamps tissue to be stapled therebetween.

The endoscopic section may be adapted for rotation about the longitudinal axis of the apparatus. Gaseous seal means located in the endoscopic section prevent escape of insufflating gas through the apparatus.

35 Claims, 19 Drawing Sheets

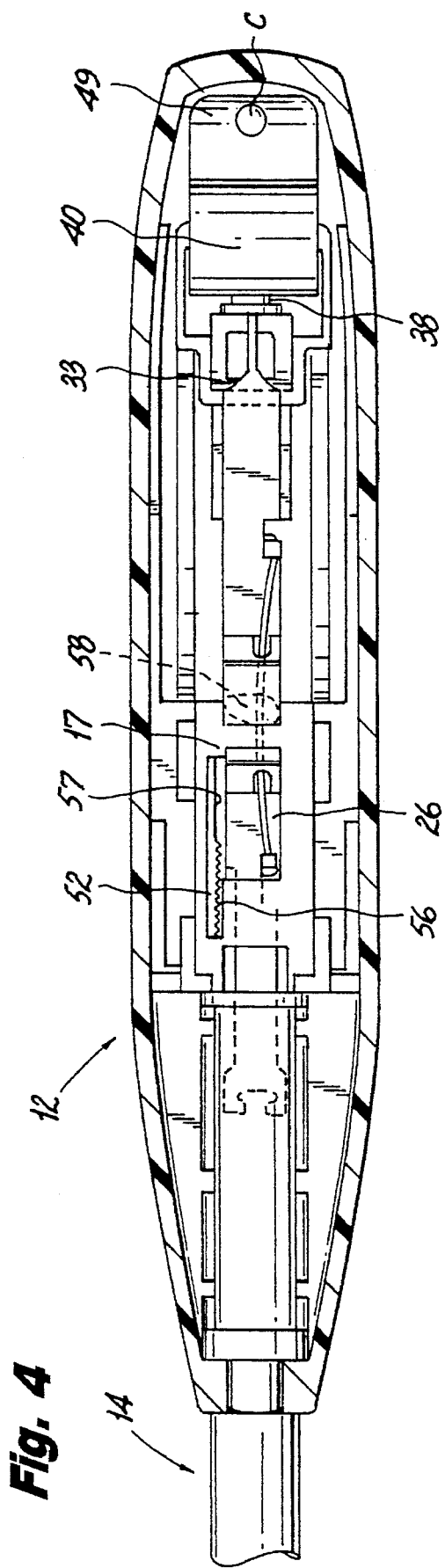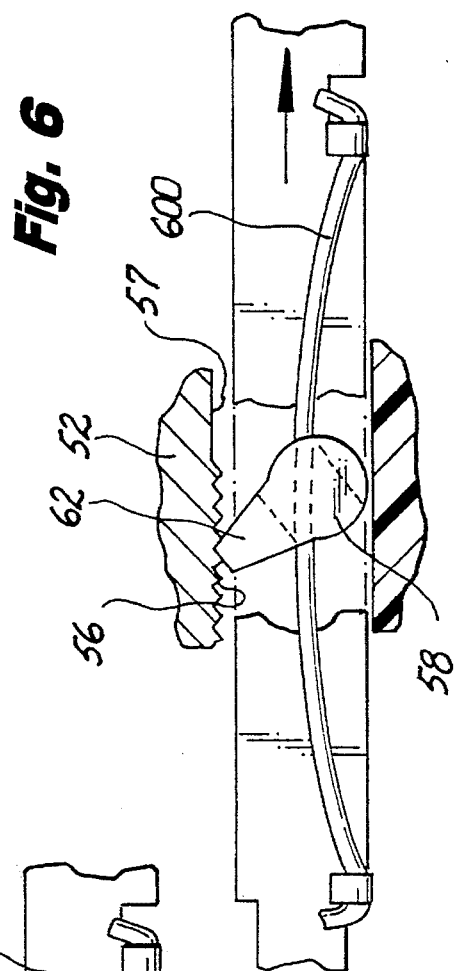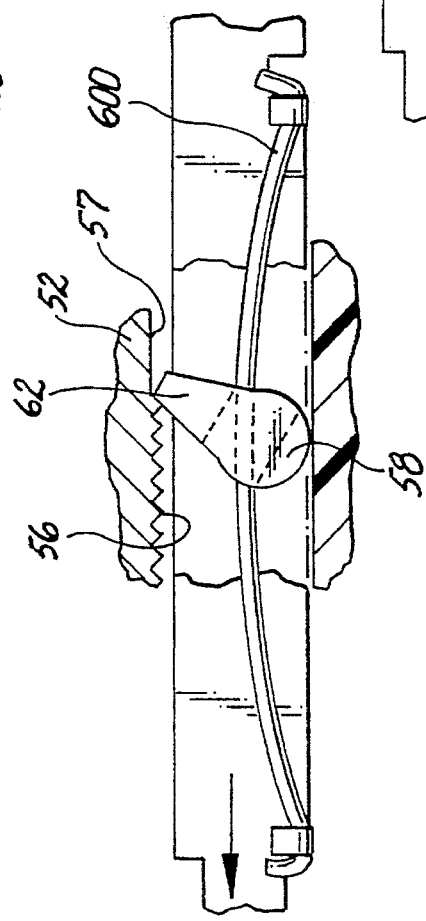

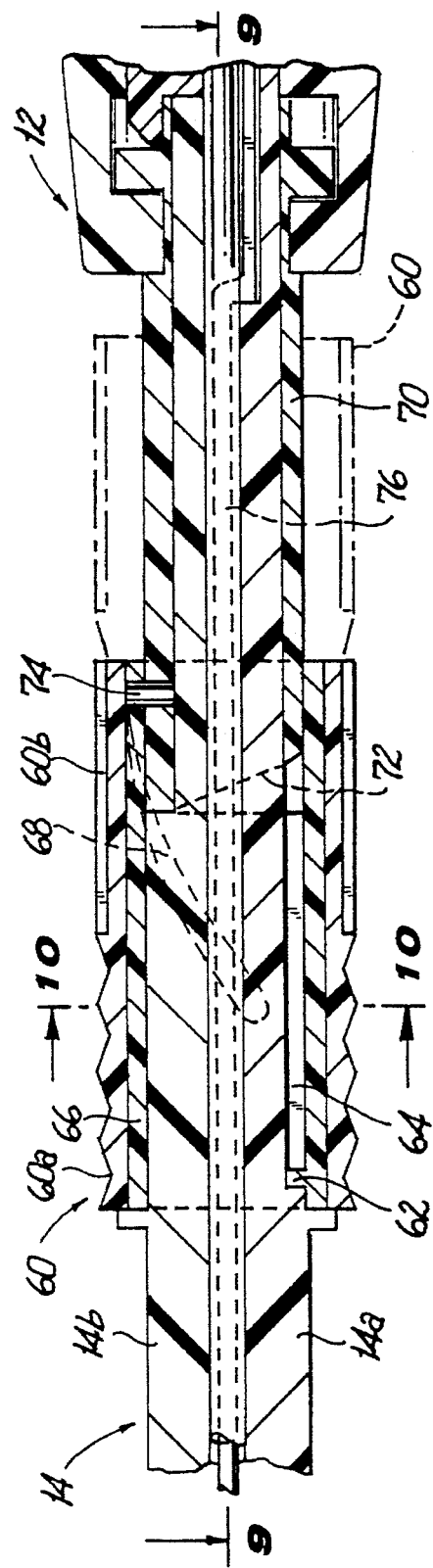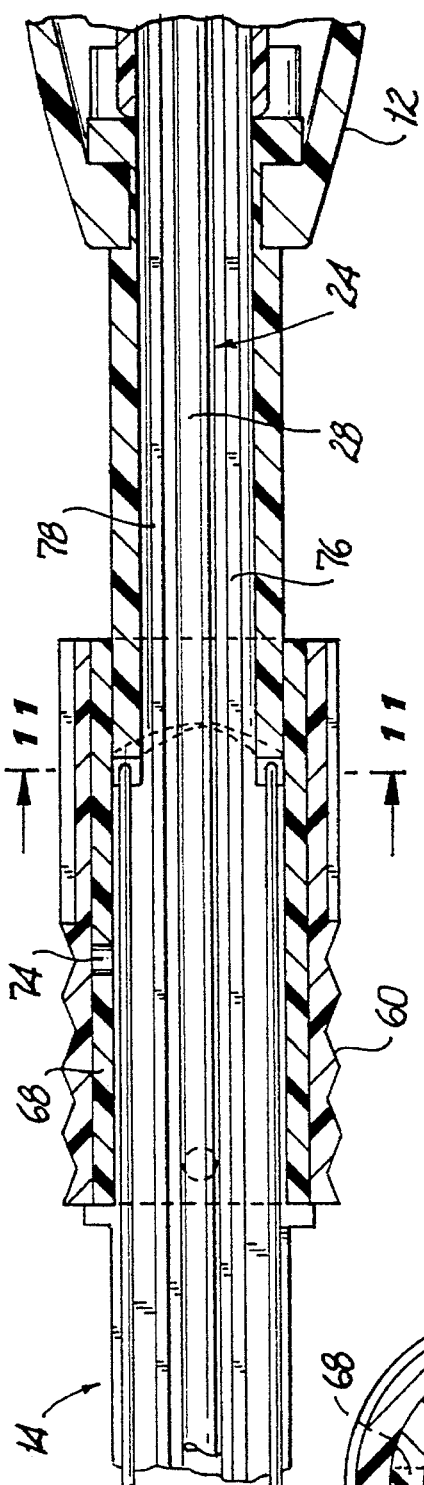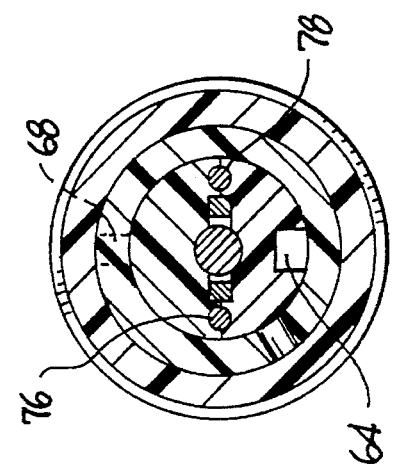

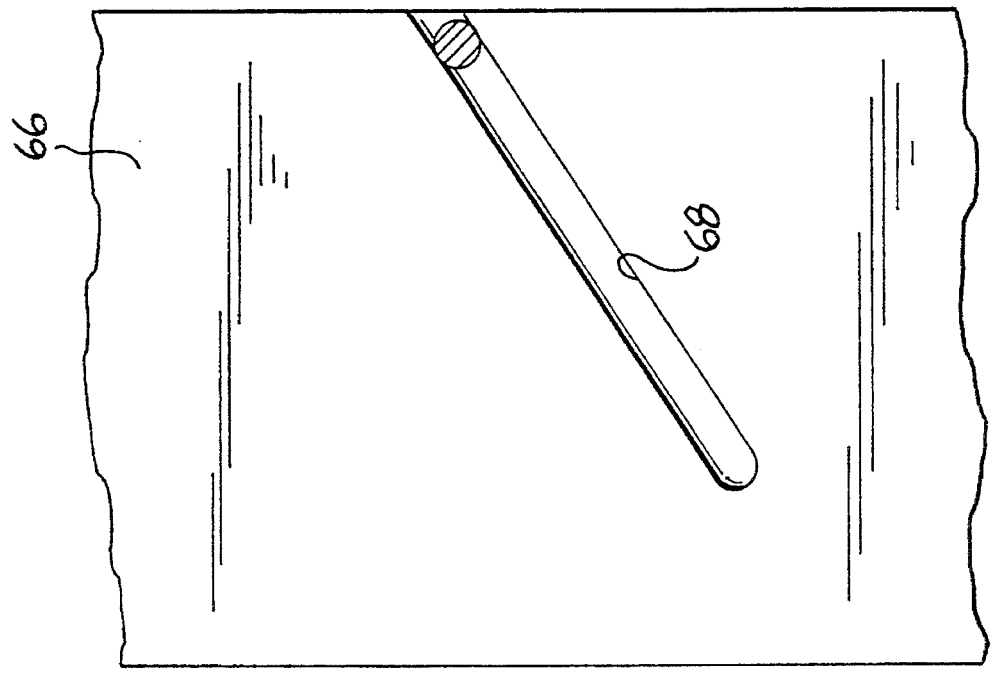
*Fig. 12*
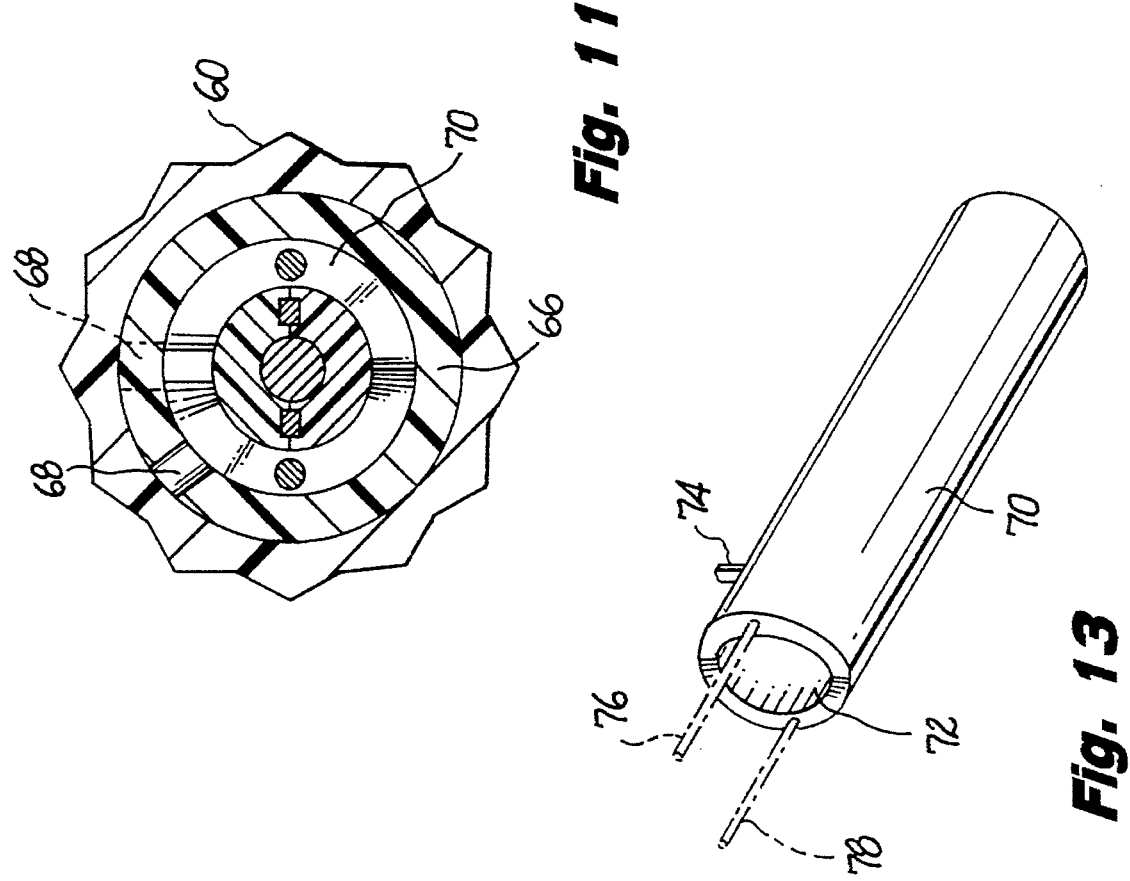
*Fig. 11*
*Fig. 13*

APPARATUS FOR ENDOSCOPICALLY APPLYING STAPLES INDIVIDUALLY TO BODY TISSUE

CROSS-REFERENCE TO RELATED APPLICATIONS

This application is a continuation-in-part of U.S. patent application Ser. No. 07/861,065, filed on Mar. 31, 1992, now U.S. Pat. No. 5,364,002, and incorporated by reference herein.

BACKGROUND OF THE INVENTION

1. Field of the Invention

The present invention relates to apparatus and methods for endoscopically applying staples individually to body tissue. More particularly, this invention relates to endoscopic surgical staplers for clamping vascular tissue and subsequently driving an individual staple through the tissue and into contact with a staple forming anvil.

2. Description of the Related Art

Surgical apparatus for applying clips to vascular tissue are well known in the art. In these devices, each leg of the clip, typically U-shaped in configuration, is held in one of the opposing jaws of the instrument and the jaws are placed on sides of the vessel. The jaws are then closed to flatten the clip to squeeze the vessel walls together to effect hemostasis. These prior apparatus suffer from the disadvantage that the clip can only be advanced into the jaws of the instrument when the jaws are open so that vessel clamping and clip closing occur simultaneously. Another disadvantage of these clip appliers is they can only be utilized to close a single vessel since they straddle the vessel; they cannot be used to attach approximated vessels or vessel portions.

Instruments for applying single staples one at a time to body tissue are also known. In contrast to clip appliers, these instruments include one jaw which contains a staple and an opposing jaw which has an anvil for deforming the legs of the staple. For example, U.S. Pat. No. 3,278,107 discloses a device where closing of the handles clamps the vessels and forms a single staple. This instrument suffers from the disadvantage associated with the above described clip appliers since clamping of the tissue and application of the staple occur simultaneously.

Some prior art surgical stapling apparatus suffer from the further disadvantage that they require invasive surgical procedures for their use, often causing excessive trauma to the patient and necessitating long post-operative recuperative periods. Invasive surgical procedures also increase the risk of complications such as bleeding, infection, organ damage, nerve damage, blood vessel damage as well as extensive scarring at the surgical site. For these reasons, the use of laparoscopic and endoscopic surgical procedures is increasing in popularity, providing additional incentive to develop the procedures further.

In laparoscopic procedures, surgery is performed in the interior of the abdomen through a small incision; in endoscopic procedures, surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated to move the tissue layers, e.g. skin, fascia, up and away from the internal body organs. Moreover, laparoscopic and endoscopic procedures often require the surgeon to act on organs, tissues and vessels far removed from the incision, thereby requiring that any instruments used in such procedures be long and narrow while being functionally controllable from the end of the instrument closest to the surgeon, i.e., the proximal end.

Because endoscopic procedures are typically viewed by means of a remote video camera, the need exists for an instrument which allows the user to first clamp tissue, view the clamped area, and decide whether to proceed with staple firing or whether to unclamp and reposition the tissue.

Up to the present there remains a need for an apparatus which is particularly adapted to endoscopically apply staples one at a time to body tissue and in which the user can unclamp and/or reposition the tissue in the engaging jaws before firing a staple. The need also exists for an instrument which, once staple firing has begun, can be withdrawn by the user only after staple formation is complete. Such an instrument could be utilized for closing individual vessels as well as for attaching approximated vessels.

SUMMARY OF THE INVENTION

The present invention overcomes the disadvantages and deficiencies of the prior art by providing a surgical stapling apparatus comprising a frame, a generally elongated endoscopic section connected to the frame and extending distally therefrom, a cartridge for storing at least one surgical staple attached to the distal end of the endoscopic section, a staple-forming anvil, means for providing relative motion between the cartridge and the anvil for clamping tissue therebetween, and pushing means for individually advancing a staple through body tissue and against the anvil. Preferably, the apparatus for endoscopic application of surgical staples stores staples in generally stacked relation to permit configuring and dimensioning the endoscopic means for insertion into an endoscopic cannula tube. The staple advancing system extends from the frame through the endoscopic section and is activated by a trigger mechanism pivotally attached to the frame and forming a part thereof.

The surgical staple storing cartridge is pivotally connected to the distal end portion of the endoscopic section through a housing member selectively pivotable by the user. Pivotal control means is located at the proximal end of the endoscopic section to pivot the housing and, consequently, the surgical staple storing cartridge from a proximal location. The location of the pivotal control means is provided for convenience and accessibility to the operator. The pivotal control means of the housing member and cartridge comprises a member movable with respect to the endoscopic section in proximal and distal directions and adapted to position the housing and cartridge at substantially zero degrees with respect to said longitudinal axis when said pivotal control means is in a first position and to position the housing and cartridge at an angle of up to about 45 degrees when said pivotal control means is in a second position.

The first position may be the proximalmost position of the pivotal control means and the second position may be the distalmost position corresponding to the staple storing means being pivoted up to about 45 degrees with respect to the longitudinal axis. Further, the pivotal control means of the staple storing means may include a generally cylindrical movable member slidably positioned about a proximal portion of the endoscopic means.

The pivotal control means of the housing and cartridge may also comprise a rotatable sleeve positioned within the movable member and adapted to rotate in a first direction when the movable member is moved toward the proximalmost position and to rotate in the opposite direction when the movable member is moved toward the distalmost position.

The surface at the distalmost end portion of the rotatable sleeve may form an angle with respect to the longitudinal axis of the endoscopic means and the distalmost end surface of the rotatable sleeve may be positioned and arranged to engage elongated control means positioned within the endoscopic section for engagement with at least a portion of the housing member at a distal location of the endoscopic section whereby rotatable movement of said rotatable sleeve correspondingly produces longitudinal movement of said elongated control means.

In a first embodiment, the elongated control means comprises at least two elongated rods positioned within the endoscopic section and in engagement with the distalmost end portion of the rotatable sleeve at the proximal ends thereof and arranged to engage at least a portion of the housing member at respectively opposed locations such that rotation of the rotatable sleeve in a first direction produces distal movement of at least one of the rods and corresponding proximal movement of the other rod. Rotation of the rotatable sleeve in the opposite direction respectively produces correspondingly respectively opposite movement of the rods. The housing member includes indentations adapted to receive each rod in engagement therewith and each rod is correspondingly configured at the distal end to engage the respective indentation to produce smooth pivotal motion of the housing member and staple storing cartridge when the rods are respectively moved distally and proximally.

In a second embodiment, the elongated control means comprises a single rod positioned within the endoscopic section and in engagement with the distalmost end portion of the rotatable sleeve at its proximal end and engaging the housing member at its distal end. Rotation of the rotatable sleeve produces pivotal motion of the housing and cartridge.

The surgical stapling apparatus of the present invention provides relative motion between the staple cartridge and the anvil to clamp tissue therebetween. Further means are provided for firing staples individually against the anvil after tissue clamping is complete. Both tissue clamping and staple firing are user controllable from a proximal location.

In a first embodiment, the means for providing relative motion between the staple cartridge and the anvil and for firing staples individually comprises a plate member positioned adjacent to and proximal of the staple to be fired. The plate member is adapted to be movable distally whereby the plate member engages and advances the staple in the distal direction. The staple is driven through clamped tissue and against a staple-forming anvil. In a second embodiment, the means for individually advancing said staples distally comprises a staple pusher mechanism whereby pusher fingers engage and advance an individual staple for driving against a staple-forming anvil.

The staple firing mechanism may include an elongated member of super elastic material such as NITINOL™ brand metal, available from Raychem Corporation, Menlo Park, Calif., and is adapted in a first embodiment to advance the staple-engaging plate member and transmit closing force thereto. In a second embodiment, the elongated member advances staples and transmits closing force through a pushing link, adapted to engage the staple pusher through pivot levers connected to the staple pusher. This member is further adapted to resiliently deform to facilitate pivoting movement to the staple storing cartridge. The staple pusher means further comprises an elongated staple firing rod.

In the preferred apparatus the staple firing mechanism is biased to a pre-fired position by a constant force negator spring which prevents the operator tendency to rotate the hand, which occurs when a spring force increases.

A trigger mechanism is pivotally mounted for pivotal movement against the force of the negator spring when pivoted proximally to a position corresponding to advancing the pusher means distally to advance the staple next in line for firing.

Means to prevent incomplete staple formation once a staple has been fired is provided. Preferably, these means comprise a ratchet and pawl system adapted to prevent proximal movement of the staple pusher means until it has been fully advanced to completely drive a staple. The ratchet and pawl means comprises a ratchet member fixedly connected to the frame means and a ribbed surface, and pawl means connected to the elongated plate advancing means and positioned adjacent the ratchet member and adapted to engage the ribbed surface. The ribbed surface is correspondingly configured and dimensioned to prevent proximal movement of the pawl means after staple firing is commenced. The ribbed surface of the ratchet member is comprised of a plurality of substantially and successive V-shaped peaks and valleys and the pawl means is configured at one end portion to engage the peaks and valleys in a manner which permits distal slidable movement thereof but prevents proximal movement thereof. Also, means is provided to release the pawl means when the pawl means is in the distalmost position corresponding to the complete firing and formation of the staple.

The frame means has a pistol-like shape and includes a first member having a distal end connected to the endoscopic section and a manual gripping member at the proximal end is adapted to be gripped manually by the user. The endoscopic section is rotatable about the longitudinal axis and the pivotal control sleeve of the housing and staple storing cartridge is connected for rotation with the endoscopic section such that rotation thereof produces corresponding rotation of said endoscopic section. As described above, distal and proximal movement thereof produces pivotal movement of the housing staple storing cartridge. The cartridge is adapted to be pivoted up to about 45 degrees with respect to each side of the longitudinal axis whereby full pivotal articulation of about 90 degrees is provided.

BRIEF DESCRIPTION OF THE DRAWINGS

Preferred embodiments of the invention are described hereinbelow with reference to the drawings wherein:

FIG. 1a is a perspective view of the distal end portion of the instrument of FIG. 1 illustrating a second embodiment of the staple storage cartridge and firing mechanism.

FIG. 4 is a cross-sectional view taken along lines 4—4 of FIG. 3 illustrating the mechanism at the proximal end of the instrument for providing controlled distal movement to advance and to close staples at the distal end.

FIG. 5 is an enlarged cross-sectional view of the pawl and ratchet system in the handle which prevents proximal movement of the staple advancing system after distal movement has begun.

FIG. 6 is a view similar to FIG. 5 illustrating the pawl and ratchet system of FIG. 5 after a staple has been fired and during the proximal movement of the firing mechanism.

FIG. 8 is an enlarged cross-sectional view taken along lines 8—8 of FIG. 1 illustrating the rotating mechanism for the endoscopic portion and the system for pivoting the staple storage cartridge from the proximal end.

FIG. 9 is a cross-sectional view taken along lines 9—9 of FIG. 8.

FIG. 10 is a cross-sectional view taken along lines 10—10 of FIG. 8 illustrating the system for providing pivotal motion of the staple storage cartridge located at the distal end.

FIG. 11 is a cross-sectional view taken along lines 11—11 of FIG. 9 illustrating further details of the system for providing pivotal motion to the staple cartridge at the distal end.

FIG. 12 is a view of the interior surface of the inner sleeve of the manually operable collar of FIGS. 8–11, projected as a flat surface to illustrate the helical groove provided for coaction with a pin to provide pivotal motion for the staple cartridge at the distal end.

FIG. 13 is a perspective view of an internal sleeve and pin which coacts with the inner sleeve shown in FIGS. 11 and 12 which forms part of the system for pivoting the staple cartridge at the distal end.

FIG. 19 is an exploded perspective view with parts separated of the staple storage and firing mechanism of the embodiment of FIG. 1a.

DETAILED DESCRIPTION OF THE PREFERRED EMBODIMENTS

General

In general, the objective of the apparatus is to store a plurality of staples in a cartridge as will be described in greater detail, and to individually fire each staple for closure against an anvil to fasten body tissue, especially vascular tissue.

Following a general description of the present instrument, the description will be divided into separate sections to describe the structure and the desired movements produced thereby. Those sections include the handle section, the staple storage cartridge pivoting system, the endoscopic section and staple firing system, and the staple storage cartridge and firing mechanism.

The Instrument

Figure 1:
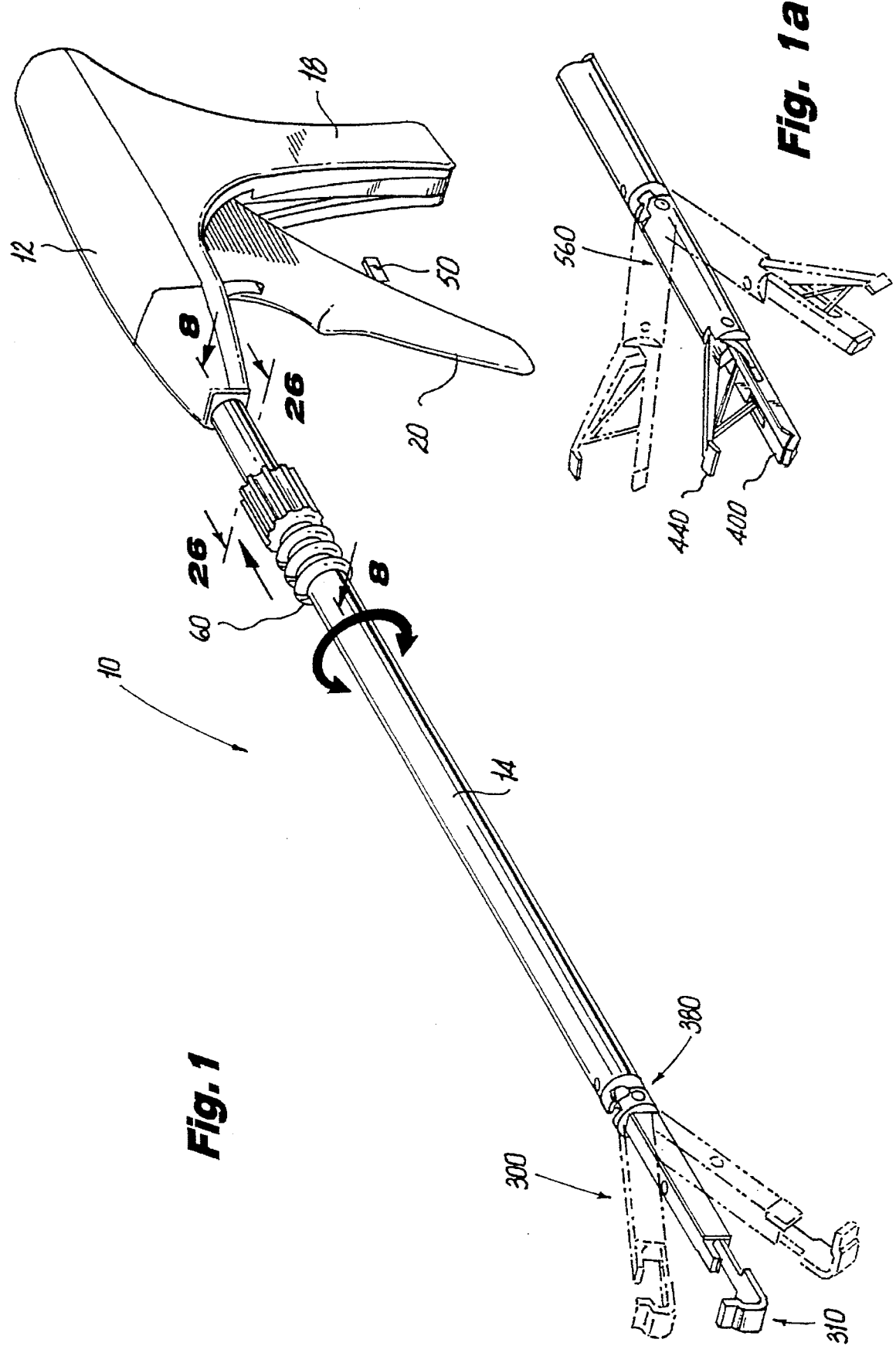
FIG. 1 is a perspective view from above, of a first embodiment of an instrument constructed according to the present invention for applying surgical staples to body tissue.

Referring initially to FIG. 1 there is illustrated in perspective view the apparatus 10 particularly adapted for endoscopic application of surgical staples to body tissue. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials will readily come to the mind of those skilled in the art.

The apparatus 10 of the first embodiment of the present invention includes handle portion 12 and an endoscopic section 14. Endoscopic section 14 has connected at its distal end portion a housing member and staple storage cartridge which pivots with respect to at least one side of the longitudinal axis extending centrally through the endoscopic section as shown in FIG. 1. Generally, the staple housing and cartridge will selectively pivot up to about 45 degrees with respect to the aforesaid longitudinal axis. In the illustration of FIG. 1 the housing and cartridge are shown in general alignment with the longitudinal axis of the endoscopic section and in phantom to illustrate a range of movement. The total range of pivotal motion of the staple storage cartridge as shown is approximately 90 degrees, i.e. 45 degrees to each side of neutral.

Referring generally to FIG. 1, the handle 12 of instrument 10 includes manual grip 18 and pivotal trigger 20 which is pivoted toward and away from manual grip 18. Trigger 20 is pivoted toward manual grip 18 during the tissue clamping and staple firing sequence which will be described in further detail. After firing, trigger 20 pivots away from manual grip 18 to return the instrument to the pre-fired condition in position for firing the staple next in line.

A double knurled finger operative collar 60 is rotatable and adapted to rotate the entire endoscopic section 14 a full 360 degrees as will be described hereinbelow, while proximal movement produces pivotal motion of the housing member and staple storage cartridge to one of the positions shown in phantom in FIG. 1a. The collar 60 may be rotated 180 degrees thereby rotating the entire endoscopic section and causing the position of the housing and cartridge to be reversed. Thus, it can be seen that the combination of full rotation of the endoscopic section and the pivotal movement of the housing member and staple storing cartridge facilitates a wide range of articulation of the staple cartridge, thus facilitating application of staples over a wide range of locations and in any of a plurality of orientations.

In the embodiment of the invention shown in FIG. 1, when the collar 60 is moved to its proximalmost position the housing and staple cartridge is in one of the positions shown in phantom in FIG. 1, i.e. at an angle with respect to the longitudinal axis of the instrument. When the collar 60 is advanced to the distalmost position the staple cartridge assumes the position shown in solid lines in FIG. 1, i.e. in alignment with the longitudinal axis of the instrument.

Thus, in the embodiment of FIG. 1, it can be seen that the full 90 degrees of movement of the housing and cartridge may be achieved simply by longitudinal movement of collar 60 in combination with full rotation of the endoscopic section. The longitudinal movement of collar 60 causes pivotal movement of the staple storing cartridge to 45 degrees in one direction and rotation of the endoscopic section provides completion of the articulation of the cartridge. Both of these movements in combination, facilitate a wide range of maneuverability of the distal end of the staple cartridge, thus facilitating application of staples over a wide range of locations and in any of a plurality of orientations.

Alternatively, in a second embodiment of the present invention, the positions of the staple cartridge may be achieved as shown in FIG. 1a, i.e. by movement of the cartridge between zero degrees and about 45 degrees on either side of the longitudinal axis. In such arrangement, to achieve the positions shown in phantom in FIG. 1a, the collar 60 is moved distally and proximally, equal distances on either side of a neutral detent. Movement in one direction would pivot the cartridge to one side and movement in the other direction would cause pivotal movement of the cartridge in the opposite direction. The directions selected would be arbitrary. However, in this last described embodiment the orientation of the cartridge would be the same throughout the 90 degree pivoting range, whereas in the embodiment of FIG. 1, the orientation of the cartridge when on one side is opposite the orientation when on the other. Further, in this embodiment the endoscopic section will be somewhat longer to accommodate the additional movement of collar 60.

The Handle Section

Figure 2:
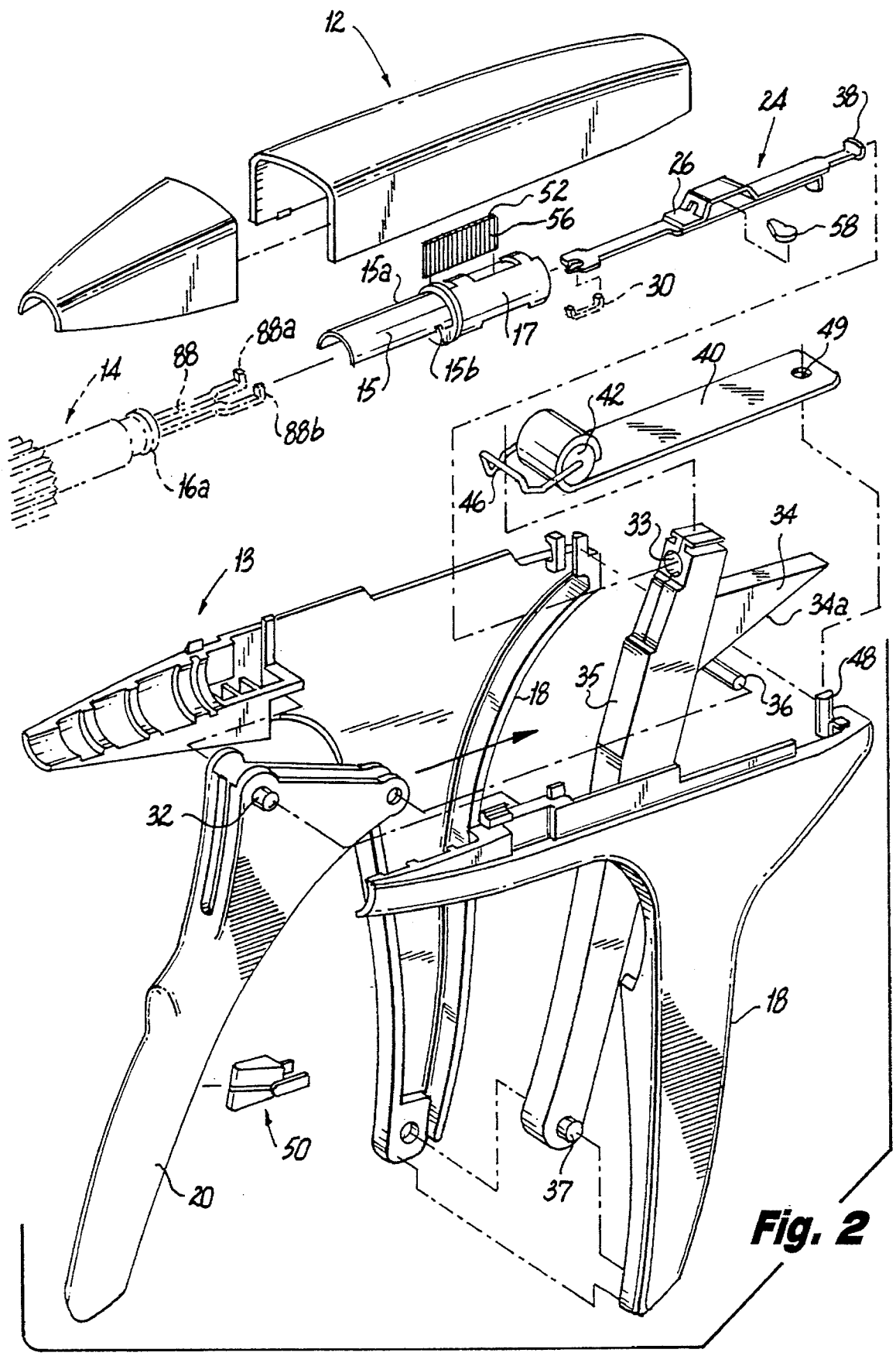
FIG. 2 is an exploded perspective view with parts separated, of the handle of the instrument of the embodiment of FIG. 1 and the associated components.
Figure 3:
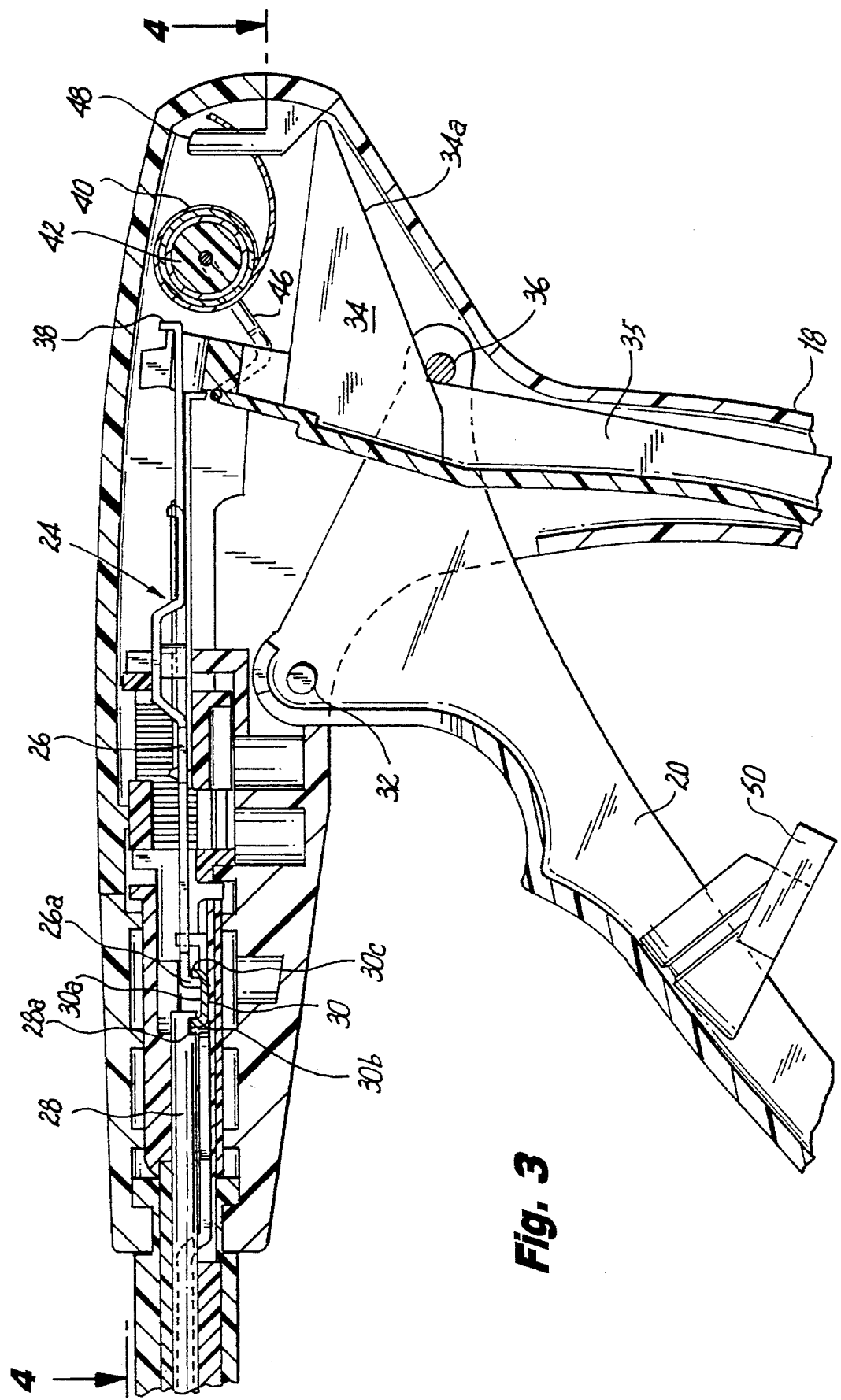
FIG. 3 is a cross-sectional view taken along lines 3—3 of FIG. 1, illustrating the handle mechanism of the instrument in the pre-fired condition.

Referring to FIG. 2, there is shown an exploded perspective view with parts separated, of the handle of the instrument with associated components. The handle is comprised of an outer housing preferably formed of separate sections as shown, of polycarbonate material. The separate parts shown are attached by welding, adhesives, etc. FIG. 3 illustrates a cross-sectional view of the handle mechanism taken along lines 3—3 of FIG. 1. The ultimate purpose of the handle mechanism is to provide controlled distal movement to the pusher assembly 24, a portion of which is shown in FIG. 2. The pusher assembly extends through the endoscopic section 14, a portion of which is shown in phantom in FIG. 2. In the embodiment shown, the endoscopic section shown is intended to be permanently and rotatably attached to the instrument via rim 16a formed on bushing 16 (FIG. 14) and rim 15a on half round sleeve 15. The instrument shown is contemplated to be entirely disposable. Half round sleeve 15 is integrally formed with barrel 17 which is in turn affixed to handle 12 at a nose piece 13.

However, it is also contemplated and within the scope of the invention to construct the endoscopic section to be selectively detachable whereby the handle may be sterilized and reused, or the endoscopic section can be sterilized, and the staple storage cartridge reloaded with staples for re-use. Alternatively a replacement staple cartridge, and optionally a replacement endoscopic section, may be detachably secured to a disposable handle for multiple use during a single surgical procedure. Thus, any combination of alternatives may be incorporated within the scope of the invention.

Figure 7:
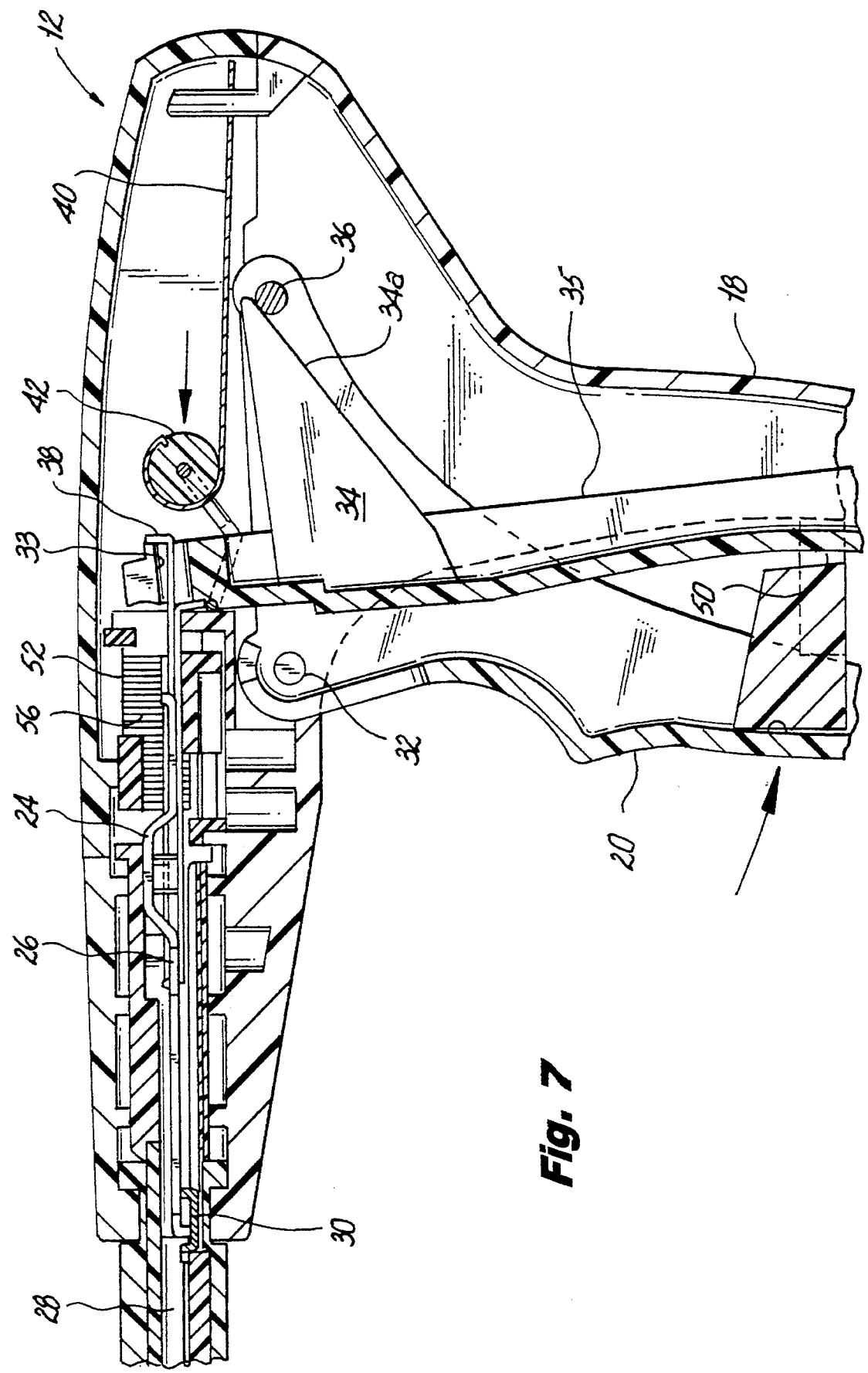
FIG. 7 is a cross-sectional view similar to FIG. 3 with the staple advancing actuating handle in the full proximal pivoted position corresponding to firing of a staple.
Figure 14:
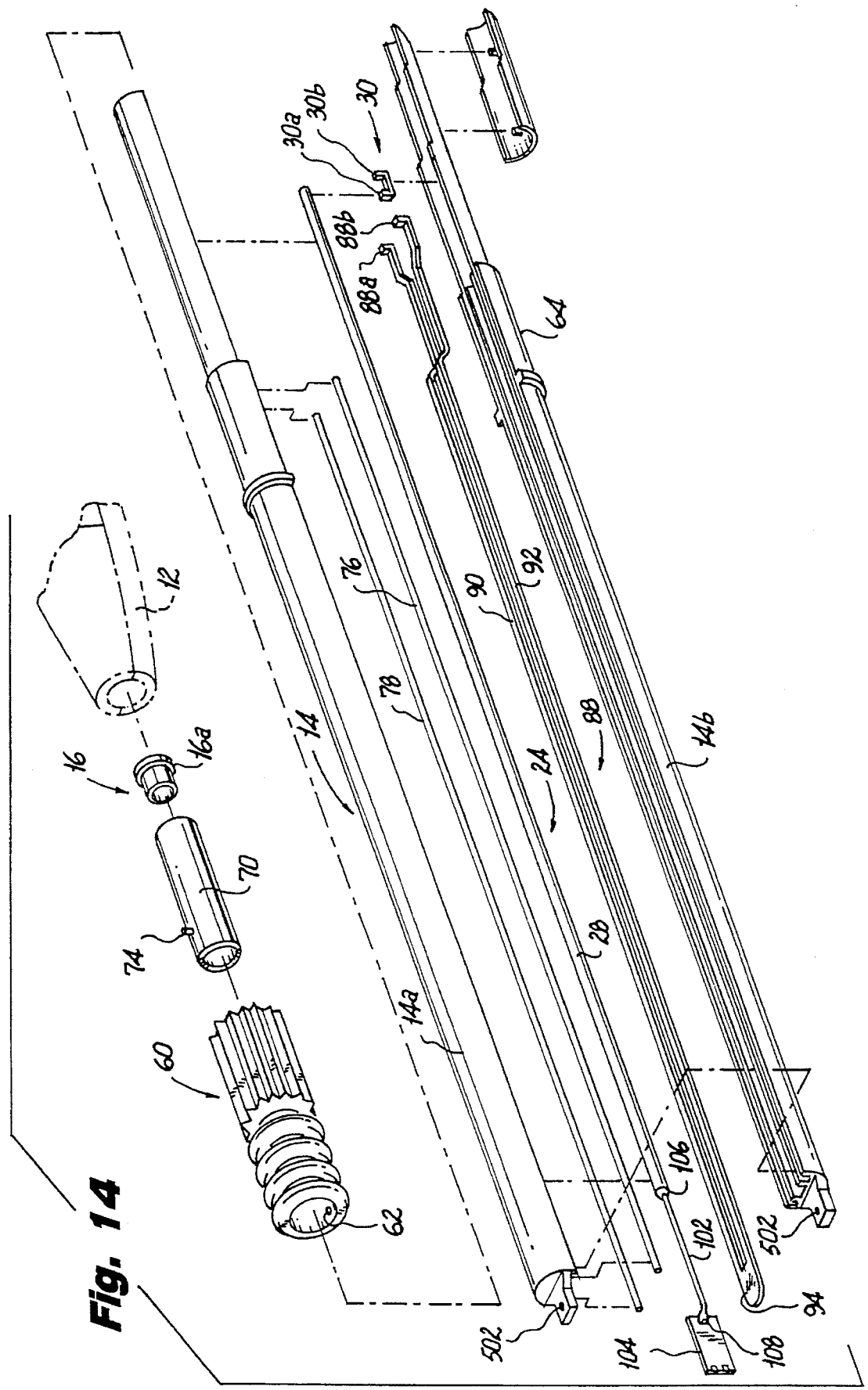
FIG. 14 is an exploded perspective view with parts separated, of the endoscopic section of the instrument of the invention, illustrating the staple advancing system and components thereof.

Referring now to FIG. 2 in conjunction with FIGS. 3, 7 and 14, pusher assembly 24 includes flanged thrust bar 26 connected to firing rod 28 by lost motion connector 30 as shown in FIG. 3. Lost motion connector 30 is a bar having a generally "U-shaped" configuration as shown. The lost motion connector 30 provides a positive connection between flanged thrust bar 26 and firing rod 28, yet provides a small space between the firing rod and the thrust bar 26 as will be described. Since the respective slots 28a and 26a in the firing rod 28 and in the thrust bar 26 are dimensioned slightly larger in width than the thickness of the legs 30b and 30c of the lost motion connector 30 which are received in these slots, a small degree of relative movement (i.e., about one tenth (1/10) of an inch) is provided permitted between the components in the staple firing chain.

This small degree of movement provides the following advantages: 1) minor pivotal proximal movements of the trigger mechanism will not immediately result in engagement between the pusher assembly and the staple next in line, thus avoiding inadvertent distal movement of the staple during handling by operating room personnel, or positioning by the user; 2) engagement of the pusher assembly with the next staple will not occur until the pawl and ratchet plate of the clutch mechanism (described hereinbelow) takes place, thus preventing inadvertent partial advancement of several staples at a time. This would occur if the operator were allowed to partially activate the trigger mechanism several times over the same part of its cycle. The clutch mechanism prevents such movements. Further, this free movement of the thrust bar 26 also permits the staple firing components to engage each other smoothly without jamming or intercomponent interference with themselves and with the components of the system for pivoting the staple storage cartridge as will be described hereinbelow. Explanation of the pivoting system for the staple storage cartridge will illustrate the advantages of the lost motion connector bar in further detail.

Trigger mechanism 20 is pivotally attached at pivot pin 32 for pivotal movement toward and away from handle grip 18, and is adapted to produce upward and downward rotational movement of triangular member 34 when horizontal pin 36, attached to trigger mechanism 20, traverses an upward arc whose center of rotation is located at pivot pin 32. Thus, when handle grip 18 is positioned in the palm of the user's hand and trigger mechanism 20 is squeezed toward handle grip 18, horizontal pin 36 traverses an upward arc while engaging the longer side 34a of triangular member 34. This movement causes triangular member 34 to rotate upward in a counterclockwise direction while upright member 35 to which it is attached, pivots forwardly about a point of rotation defined by pivot pin 37 located at the lowermost end of a handle grip 18 shown in FIG. 2.

As can be seen in FIGS. 2 and 3, pusher assembly 24 is connected to upright member 35 through aperture 33 such that inward squeezing of trigger mechanism 20 will cause the entire pusher assembly to advance distally against the constant force provided by negator spring 40 as shown. The negator spring 40 is formed of a resilient flat spring material coiled about the rotational bar 42 which is rotationally mounted about cross member 44 which forms part of bracket 46. The free end of negator spring 40 is attached to an anchor pin 48 via aperture 49 as shown, while the spring 40 is normally biased toward the coiled configuration as shown in FIG. 3. It can therefore be appreciated that after squeezing trigger mechanism 20 the full stroke from the position shown in FIG. 3 toward handle grip 18 to the position shown in FIG. 7, release of the trigger mechanism will permit the negator spring 40 to assume control and to return rotational bar 42 to the pre-fired proximal location by the automatic winding action of the negator spring 40 to its original unloaded configuration. This motion in turn causes the entire pusher assembly 24 to return to the proximalmost pre-fired position as shown in FIG. 3. The constant force of negator spring 40 uniquely prevents the natural tendency of the user to rotate the hand as with springs which increase in force when progressing through a full spring cycle.

Referring once again to FIGS. 2 and 3, trigger stop device 50 is attached to trigger mechanism 20 and is configured and dimensioned for engagement with handle grip 18 in a manner to thereby limit the proximal pivotal movement of trigger mechanism 20. Depending upon the particular limits required in the apparatus, trigger stop device 50 can be dimensioned accordingly.

Referring now to FIGS. 4–6, the structure and function of the uni-motion clutch mechanism will be described. This clutch mechanism prevents proximal movement of the pusher assembly in the event the trigger mechanism is released during staple firing but before the full firing stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring now to FIG. 4 in conjunction with FIGS. 5 and 6, ratchet plate 52 is fixed to barrel 17 and therefore fixed with respect to the handle housing and possesses a surface defined by a plurality of right angle triangular shaped parallel teeth 56 as shown in FIGS. 4–6. Pawl 58 is rockably mounted for distal and proximal movement with pusher assembly 24 through barrel 17, and is biased toward ratchet plate 52 by resilient wire spring 600 as shown. Ratchet plate 52 further includes a non-ratcheting surface, 57, which does not engage the pawl during the initial clamping phase of the stapling stroke. The location of pawl 58 shown in FIG. 4 corresponds to the pre-fired condition of the apparatus with negator spring 40 in the fully wound position and pawl 58 located proximal of ratchet plate 52. Further, pawl 58 is preferably of stainless steel while ratchet plate 52 is made of brass or other compatible material.

While trigger mechanism 20 is squeezed toward handle grip 18 producing distal motion of the entire pusher assembly 24, relative motion between the staple storing cartridge and the anvil clamps tissue to be stapled, described hereinbelow. No staple firing occurs during this first movement of the stapling apparatus. During further squeezing of the trigger mechanism, the staple firing mechanism is actuated. When the staple firing mechanism is actuated, pawl 58 engagably slides distally past the ratchet surface 57 of ratchet plate 52 as shown in FIG. 5 such that one corner of the tip 62 of the pawl 58 sequentially engages each tooth 56 of ratchet plate 52 to thereby prevent proximal movement of the pusher assembly in the event the trigger mechanism is released by the operator. The engagement of pawl 58 with ratchet plate 52 provides audible confirmation that the pusher assembly is moving distally and a staple is being fired since the user will hear a series of progressive audible clicks. This action continues with the tip 62 of pawl 58 sliding past the ratchet surface of the ratchet plate 52 until the pawl is positioned distally of the distalmost tooth as shown in FIG. 5. Pawl 58 engages ratchet plate 52 only during staple firing. Thus, the user is free to release trigger mechanism 20 to unclamp tissue held between the cartridge and anvil and reposition the stapling apparatus.

After completion of the staple firing stroke and upon release of the trigger mechanism 20 the pawl 58 moves proximally with the pusher assembly as described under the action of spring 40. The end portion 62 of pawl 58 which is now free, engages the distal end of the ratchet plate 52 causing the pawl to rock to the reverse direction shown in FIG. 6 so as to slide proximally past the ratchet surface of ratchet plate 52 without interference to the proximal movement of the pusher assembly 24. Thus, the clutch mechanism as described will effectively permit squeezing the trigger mechanism 20 toward the handle grip 18 during actuation of the staple firing mechanism while maintaining all positions midway through the firing stroke in the event the operator releases the grip, while permitting return motion thereof after the stroke has been completed. Thus, the clutch mechanism advantageously prevents partial staple formation by requiring a complete firing stroke once the decision to fire a staple has been made.

The Staple Storage Cartridge Pivoting System

Referring to FIGS. 8–14, the system for pivoting the staple storage cartridge and housing member located at the distal end of the endoscopic section 14 will now be described. FIG. 8 illustrates double knurled finger operable collar 60 which is mounted for rotation with the endoscopic section 14 by inwardly extending pin 62 which is slidably positioned within longitudinal groove 64 in the outer housing half section 14a of endoscopic section 14, as shown in further detail in FIG. 14. Thus collar 60 is readily slidable distally and proximally while pin 62 slides within groove 64. Thus while permitting slidable movement of collar 60, pin 62 prevents independent rotation of collar 60 relative to the endoscopic section 14. Accordingly, when collar 60 is gripped between the user's fingers and rotated, the endoscopic section 14 rotates with the collar.

Positioned within finger operable collar 60 is helically grooved inner sleeve 66 fabricated of a suitable plastic material such as nylon, glass filled for strength. Helically grooved inner sleeve 66 is generally cylindrical in shape and includes a helical groove 68 shown in phantom lines in FIG. 8 and illustrated schematically in the projected frontal view of the sleeve shown in FIG. 12. The sleeve 66 is fixedly attached to outer collar 60 for rotation therewith. In the projected view of FIG. 12, the helical groove appears as a diagonal groove having a linear shape. In FIG. 11, finger operable collar 60 is shown in cross-section and the inner helically grooved sleeve 66 is shown whereby helical groove 68 is represented at two locations as viewed in FIG. 11. In FIG. 11, the cross-section of groove 68 at the 10 o'clock position (where lines 11—11 are located in FIG. 9) is just distal of the cross-section of groove 68 shown in phantom at the 12 o'clock position.

Referring now to FIG. 8 in conjunction with FIGS. 9–13, elongated internal cylindrical sleeve 70 is positioned partially within inner helically grooved sleeve 66 and collar 60 when collar 60 is in the distalmost position, as shown in FIG. 8; however, when collar 60 is withdrawn to the proximalmost position as shown in phantom lines in FIG. 8, the major portion of internal cylindrical sleeve 70 is positioned within collar 60 as shown. Internal sleeve 70 is preferably of nylon (preferably glass filled for strength) and defines a distal face 72 which is generally oriented at an acute angle with respect to the longitudinal axis of the instrument as shown clearly in FIGS. 8 and 13. The sleeve 70 contains pin 74 extending radially outwardly from the outer surface as shown. Pin 74 is preferably of steel or it may be formed of nylon integral with sleeve 70. Pin 74 is positioned for slidable movement within the helical groove 68 of inner sleeve 66 of collar 60 such that proximal movement of collar 60 will cause pin 74 to follow the groove 68 causing sleeve 70 to rotate in one direction. Similarly, distal movement of collar 60 to the position shown in phantom lines in FIG. 7 will cause pin 74 to traverse groove 68 in the opposite direction thereby causing sleeve 70 to rotate in the opposite direction.

The significance of the rotational motion of sleeve 70 as it pertains to the pivotal motion of the staple storing cartridge will be described in further detail hereinbelow. At this stage, however, it is sufficient to state that the obliquely oriented distal face 72 of sleeve 70 engages the proximal ends of a pair of longitudinally extending push rods 76,78 shown in phantom lines in FIG. 13 and more clearly in FIG. 14 such that when collar 60 is moved distally or proximally, inner sleeve 70 also rotates and the rods 76,78 respectively move in equal and opposite directions by the engagement with different portions of oblique distal face 72 with these rods. In essence, one rod is engaged by a surface portion distal of the surface portion on the side of face 72 which engages the other rod. Thus, when the sleeve 70 is rotated in one direction, rod 78 moves in the distal direction while rod 76 withdraws proximally the same distance, and when sleeve 70 is rotated in the opposite direction, rod 76 moves in the distal direction and rod 78 moves proximally the same distance.

Collar 60 contains rotary ridges 60a in the distal half and longitudinal ridges 60b in the proximal half, and is thus conveniently movable longitudinally and rotatably by the user when the appropriate knurled portion is gripped between the user's fingers. However, the operator need not grip the collar 60 at any specific locations. The ridges may be formed integral by molding procedures or alternatively may be in the form of knurled surfaces. The rotary ridges respectively permit collar 60 to be finger movable distally and proximally, while the longitudinal ridges assist in rotation of collar 60 by hand. Rotational motion of the collar causes the endoscopic portion 14 to rotate while proximal movement of the collar in a preferred embodiment causes the staple storing cartridge to pivot up to about 45 degrees in one direction with respect to the longitudinal axis of the instrument as shown in FIG. 1.

Distal movement of the collar 60 to the distalmost position shown in FIG. 8, causes the staple storing cartridge to withdraw to the original orientation shown in FIG. 1 which is generally in line with the endoscopic section. Thus, by pivoting the staple storing cartridge up to 45 degrees and by rotating the endoscopic portion 14, the total range of movement of the staple storing cartridge is 45 degrees to either side of the endoscopic section traversing a total of 90 degrees of effective pivotal movement. With respect to movements of collar 60, the direction which produces pivotal motion of staple storage magazine 16 away from the longitudinal axis or toward the axis is clearly a matter of choice and would be determined by the respective configurations of the coacting components.

Figure 15:
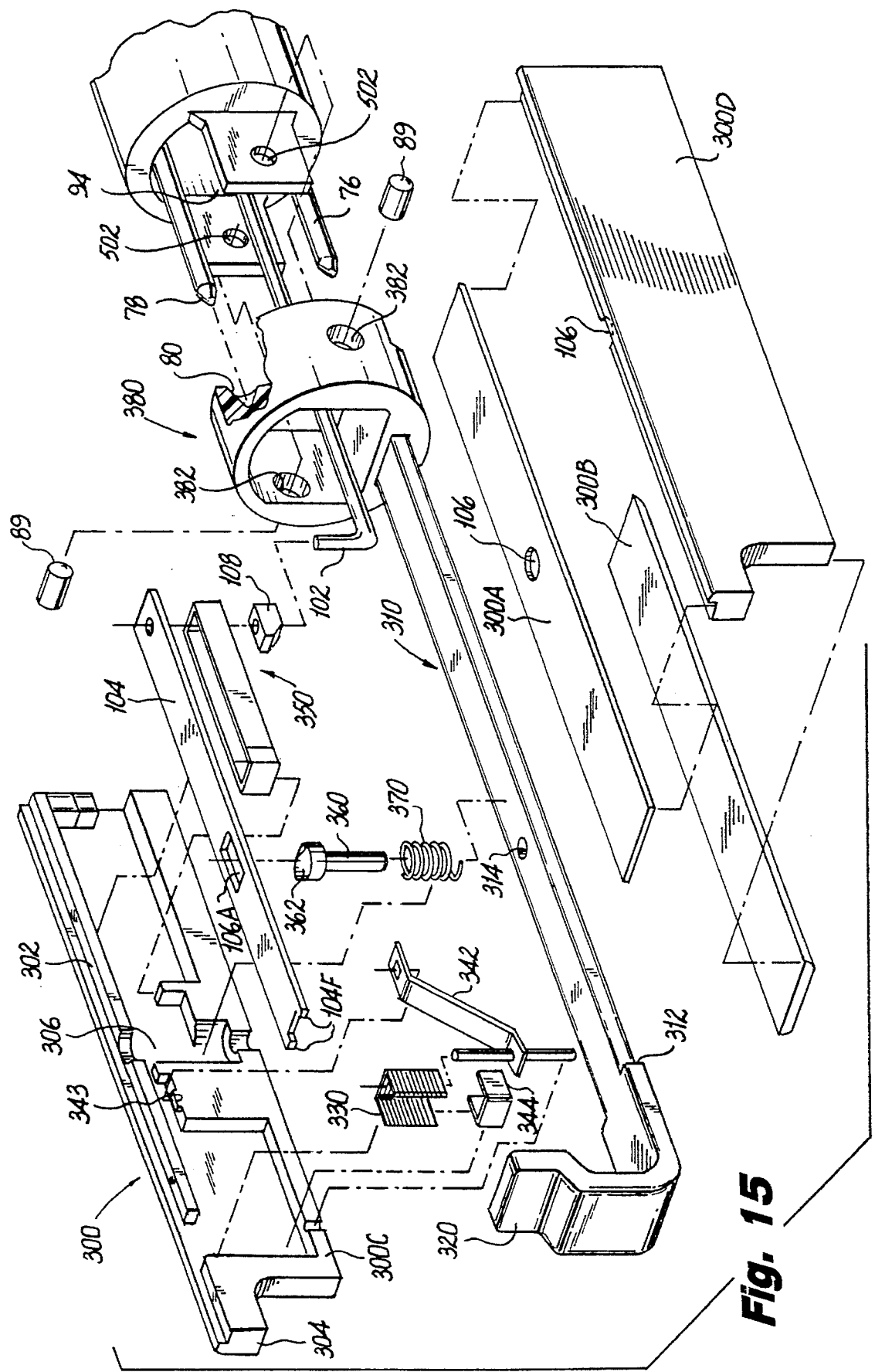
FIG. 15 is an exploded perspective view with parts separated of the staple storage and firing mechanism of the first embodiment of the present invention.
Figure 16:
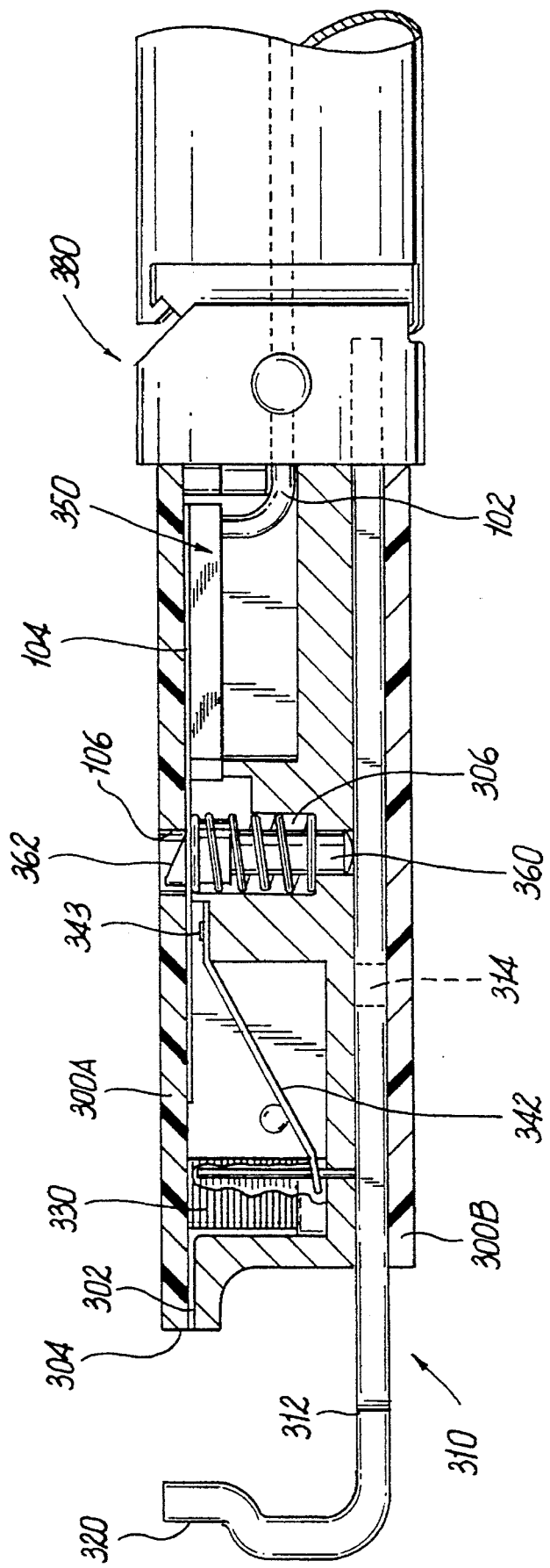
FIG. 16 is a side view in partial cross-section showing the staple storage and firing mechanism of FIG. 15 with the anvil jaw in an open position.

Referring now to FIG. 15, the system for providing pivotal motion to the staple storing cartridge according to one embodiment of the present invention is illustrated. In FIG. 15 the staple storage cartridge is shown in the position generally in alignment with the endoscopic section of the instrument. The staple storage cartridge 300 is slidably mounted to anvil 310. Anvil 310 is fixedly mounted to housing 380 to be selectively pivotal therewith. The distal ends of endoscopic half sections 14a and 14b are pivotally connected to housing 380 through apertures 502. Apertures 502 align with housing apertures 382 to receive pivot pins 89.

The upper housing section contains an indentation 80 having a "V-shaped" cross section and the lower housing section contains a similar indentation also having a "V-shaped" cross section as shown. Both indentations are adapted to respectively engagably receive the rounded distal ends of rods 76, 78. When the rods are respectively and alternately moved in the proximal and distal directions as described hereinabove, one rod may advance distally and the other rod withdraws to permit the pivotal motion of housing 380 and anvil 310 which is engaged therein. Consequently, pivotal motion of anvil 310 causes staple storage cartridge 300 to pivot therewith.

When the collar 60 is moved, rod 76 moves distally into indentation 80 to engage the lower housing section and rod 78 withdraws to accommodate the pivotal movement of anvil 310 and staple storing cartridge 300 upward as shown in phantom in FIG. 1.

Alternatively one rod may be provided and connected to the housing member and adapted to pivot the housing member by causing such rod to move proximally and distally thereby actually pivoting the housing member about the pivot point.

Figure 20:
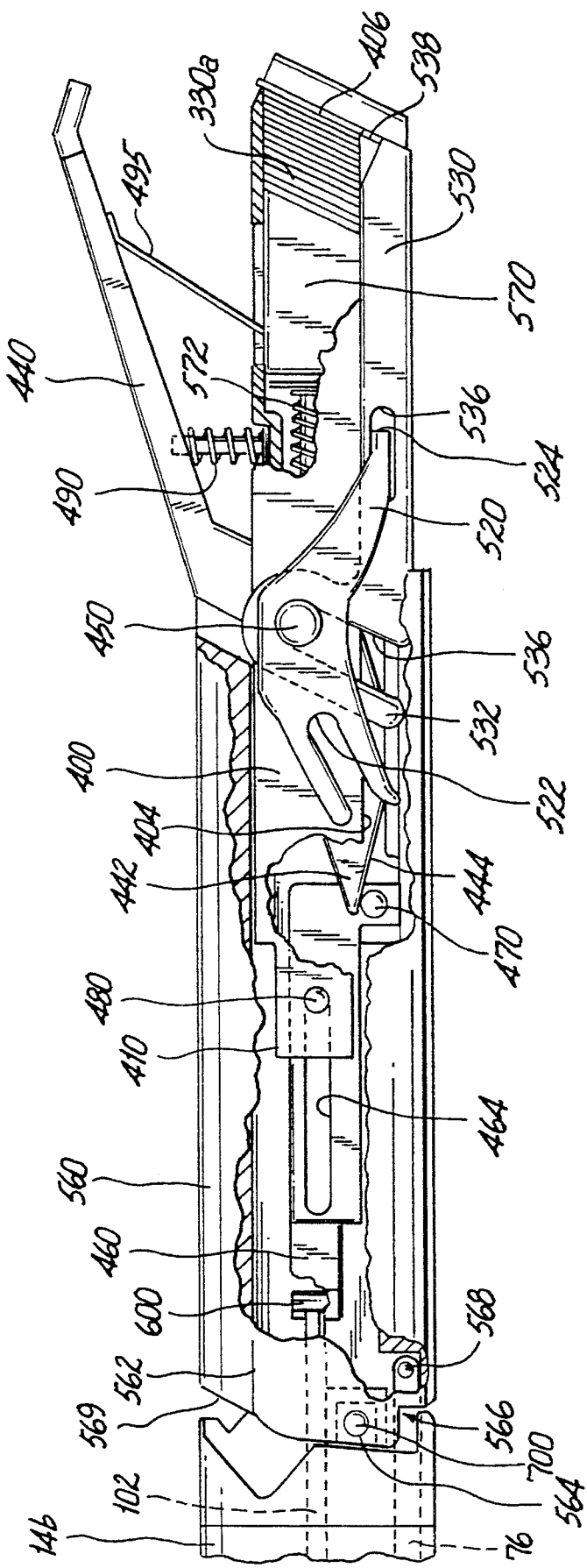
FIG. 20 is a side view in partial cross-section showing the staple storage and firing mechanism of FIG. 19 with the anvil jaw in an open position.
Figure 21:
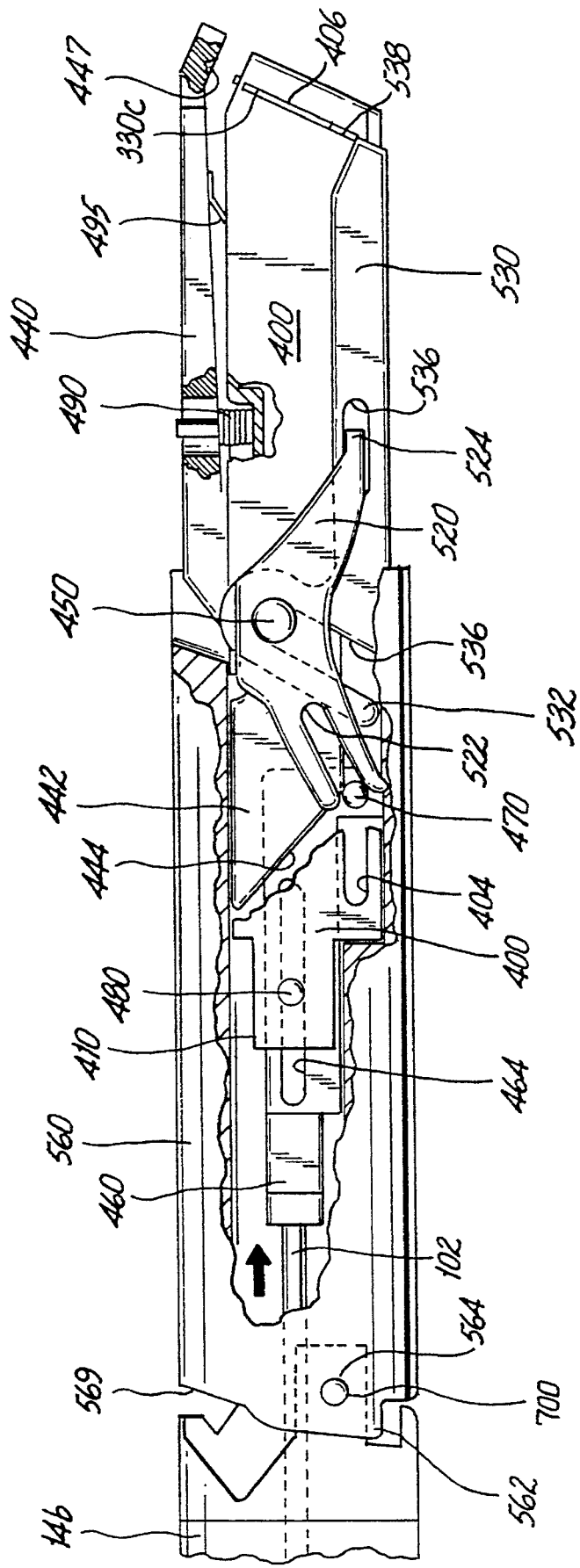
FIG. 21 is a side view in partial cross-section showing the staple storage and firing mechanism of FIG. 19 with the anvil jaw in a closed position.
Figure 22:
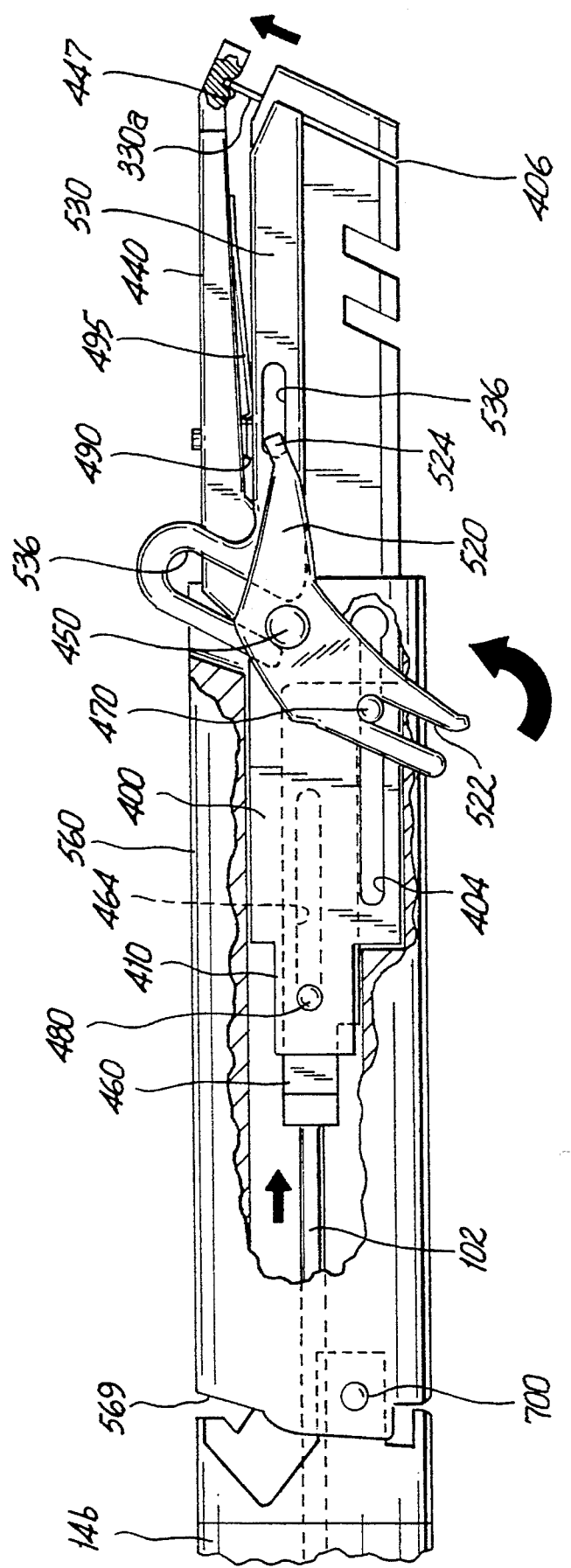
FIG. 22 is a side view in partial cross-section showing the staple storage and firing mechanism of FIG. 19 in the process of firing a staple.

Referring now to FIG. 20, the system for providing pivotal motion to the staple storing cartridge according to a further embodiment of the present invention is illustrated. The staple storage cartridge 400 is shown in the position generally in alignment with the endoscopic section of the instrument. The staple storage cartridge 400 is mounted to cartridge housing arms 562 of cartridge housing member 560 such that it is pivotal therewith.

To pivot the housing and staple storage cartridge, housing member arms 562 contain a channel 566 for receiving rod 276. Rod 276 pivots housing 560 through pivotal connection 568. When collar 60 is moved proximally, rod 276 moves distally, pivoting housing 560 and, consequently, staple storage cartridge 400. Upper proximal edge 569 of housing 560 is angled to facilitate the upward pivotal motion of the housing member. Proximal edge 569 is received by the distal end of the endoscopic section when the housing member is fully articulated.

The Endoscopic Section

Referring back to FIG. 14 the endoscopic section is shown in exploded view with parts separated for convenience of illustration. As noted above, the endoscopic section may be permanently rotatably attached to handle 12 as shown in a disposable instrument; alternatively as noted above, it may be removably rotatably attached to a re-usable handle, or a variety of other combinations or configurations. Endoscopic section 14 includes upper housing half section 14a and lower housing half section 14b. The housing half sections are preferably of a polycarbonate material such as LEXAN brand material mentioned previously, and are attached by welding, adhesives, etc. Positioned within the upper and lower housing half sections is pusher assembly 24 as described in more detail below, and support member 88, formed of stainless steel and having a pair of elongated legs 90, 92 which are joined at 94 at the distal end and which contain upwardly extending feet 88a, 88b at the proximal end. As shown in FIG. 15, support member 88 is attached at the distal end 94 to the staple storing cartridge housing member by pivot pins 89 where the housing is pivotally attached. The proximal connection points of support member are best illustrated in FIG. 2 wherein upwardly bent feet 88a, 88b are positioned within slots 15b in half round collar 15 which is fixedly attached to handle housing 12 by barrel 17 and nose piece 13 and related members provided therein.

Support member 88 is fabricated of stainless steel and its purpose is to stabilize the dimension of the endoscopic section 14 to prevent the forces acting on the components from stretching or compressing the upper and lower housing half sections 14a, 14b of the endoscopic section which are constructed of a polycarbonate material such as LEXAN brand material. Thus, the support member 88 provides dimensional stability to the endoscopic section while the endoscopic section is supporting the components being subjected to forces for supporting, advancing and forming the surgical staples as will be described.

Figure 26:
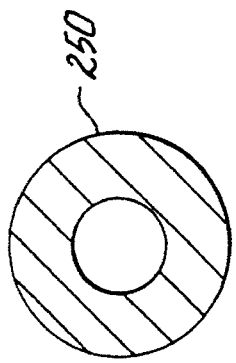
FIG. 26 is a cross-sectional view taken along lines 26—26 of FIG. 1, schematically illustrating gaseous seal means for the endoscopic section portion of the instrument of the present invention.

The endoscopic section of the surgical stapling apparatus further includes gas seal means 250 as depicted in FIG. 26.

FIG. 26 is a cross-sectional view taken along lines 26—26 of FIG. 1, illustrating schematically a gaseous seal means in the form of silicone grease 250 to prevent the insufflating gaseous media from escaping from the patient's body cavity through the instrument. Such gaseous seal means may alternatively be in the form of a separate seal block positioned within the endoscopic section, or it may alternatively be in the form of a gaseous sealing block located either in another portion of the endoscopic section or alternatively in the handle section.

The Staple Firing System

Referring further to FIG. 14, the staple pusher assembly 24 of a first embodiment of the present invention is illustrated. Staple pusher assembly 24 is formed of firing rod 28 connected to flexible elongated firing wire 102 which is in turn connected to pusher plate assembly 104 as shown. The connection between firing rod 28 and firing wire 102 is a crimped or swaged connection at 106, whereas the connection between firing wire 102 and pusher 105 is accomplished by an interference fit between the firing wire 102 and collar 108 which is attached to pusher plate 104. Firing rod 28 and pusher plate 104 are preferably made of stainless steel whereas firing wire 102 is made to be resiliently flexible to accommodate the pivotal movement of the staple storing cartridge since firing wire 102 is located within the instrument at the location of staple cartridge. In particular, firing wire 102 is preferably made of a super elastic metal. One example of such super elastic metal is NITINOL brand metal referred above. This material has a reduced tendency to fatigue after a substantial number of cycles of deflection caused by pivoting the staple storage cartridge. Other resilient materials are also contemplated for firing wire 102.

In a second embodiment of the present invention, staple pusher assembly 24 comprises firing rod 28 connected to flexible elongated firing wire 102 through crimped or swaged connection 106 as in the previous embodiment. However, at its distal end, firing wire connects to a pushing link 460 rather than the pusher plate of the first embodiment. This pushing link actuates the staple firing mechanism, described hereinbelow.

Staple Storage Cartridge and Firing Mechanism

Referring to FIGS. 15–18, there is illustrated a first embodiment of the staple storage and firing mechanism of the present invention. The mechanism comprises a staple storing cartridge 300 slidably mounted to anvil body 310. Cartridge 300 has a top wall 300A and bottom wall 300B both glued, welded or otherwise attached to sidewalls 300C, D. The proximal end of anvil 310 is fixedly mounted to housing 380 and is selectively pivotal therewith by movement of finger ring 22 as previously described. The distal end of anvil body 310 extends anvil head 320, perpendicular to the longitudinal axis of anvil 310. Anvil head 320 cooperates with distal end 304 of cartridge 300 to clamp tissue to be stapled.

Cartridge 300 is adapted to hold a plurality of staples 330 in a vertical stacked array. To drive a staple from the vertical stacked array through clamped tissue, channel 302 is formed in the staple storing cartridge. Staples are fed to cartridge channel 302 by staple follower 344 which abuts the lowermost staple in the vertical stacked array. Spring 342, mounted by fastener 343 to the staple cartridge 300, urges staple follower 344 upward. Follower 344 distributes the upward force of spring 342 to the stack of staples, positioning the uppermost staple into channel 302 to be fired.

Figure 18:
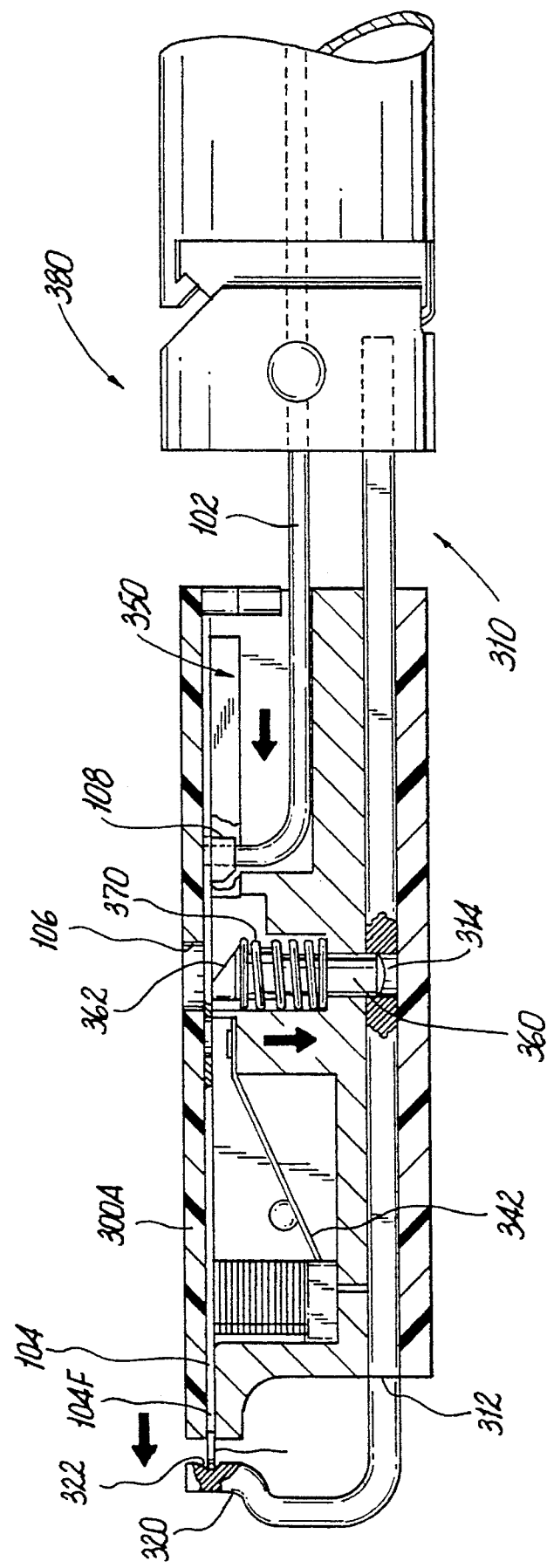
FIG. 18 is a side view in partial cross-section showing the staple storage and firing mechanism of FIG. 15 in the process of firing a staple.

Anvil head 320 comprises staple forming cups 322, shown in FIG. 18, for deforming and closing the legs of staple 330. Anvil body 310 includes a shoulder 312 and a locking pin-receiving aperture 314. Shoulder 312 and aperture 314 cooperate to provide a distal end point for cartridge 300 when it slides along anvil body 310 for tissue clamping and staple firing.

Staple 330 is ejected through channel 302 by staple firing mechanism 350. Firing mechanism 350 comprises pusher plate 104 for both advancing staple cartridge 300 to clamp tissue and for driving a staple through clamped tissue and against staple forming cups 322. To actuate pusher plate 104, firing rod 28 connects to the pusher plate through elongated, resiliently flexible firing wire 102, previously described. The distal end of pusher plate 104 terminates in fingers 104F for engaging the staple 330 to be fired.

Pusher plate 104 includes means to advance the staple cartridge distally to clamp tissue against anvil head 320 prior to staple firing. These means include aperture 106 for engaging a locking pin 360. Locking pin 360, coaxially disposed within compression spring 370 and having angled camming surface 362, is positioned within cartridge orifice 306.

Figure 17:
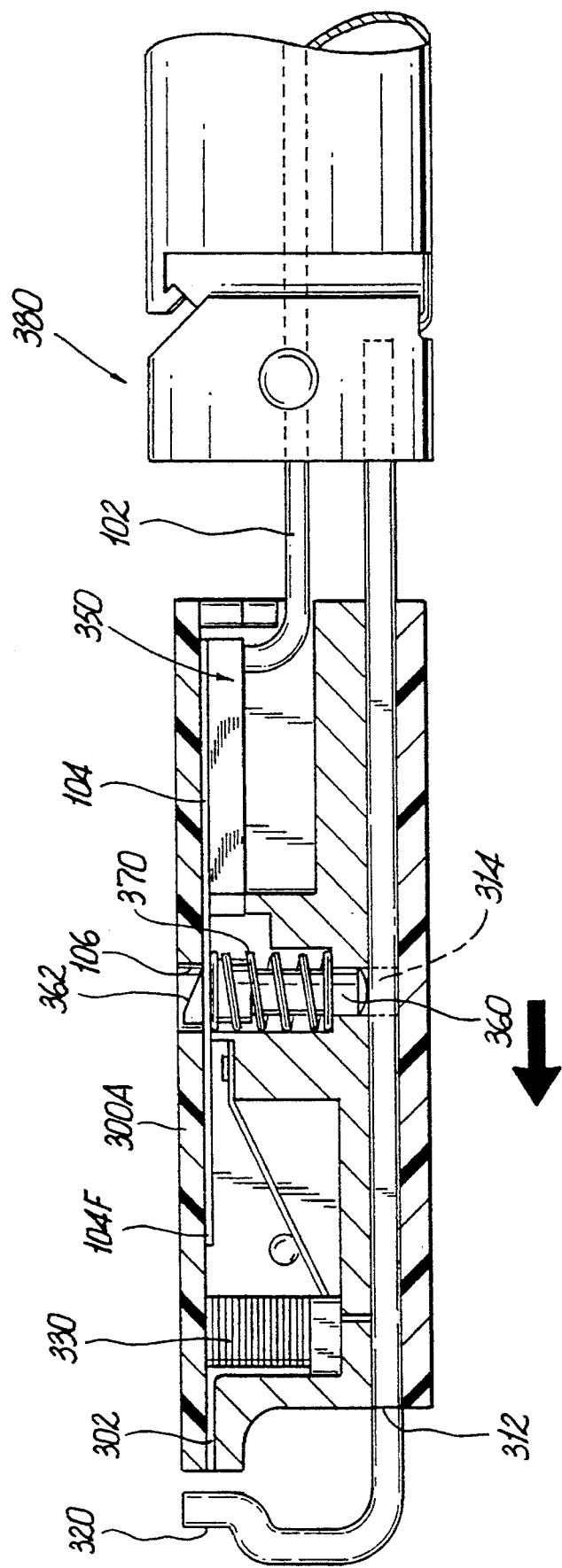
FIG. 17 is a side view in partial cross-section showing the staple storage and firing mechanism of FIG. 15 with the anvil jaw in a closed position.

In the operation of the surgical stapling apparatus of FIG. 15, approximation of handles 18 and 20 (FIG. 1) advances firing wire 102 distally as shown in FIG. 17. The force of firing wire 102 against pusher plate 104 is transmitted to locking pin 360 through pin-engaging aperture 106A. Because the lowermost end of locking pin 360 does not align with any aperture in anvil 310, the locking pin is constrained in aperture 106A and cartridge orifice 306. The firing force thus causes locking pin 360 to move distally.

During actuation of pusher plate 104, engagement of the locking pin 360 with apertures 106, 106A and cartridge orifice 306 causes the cartridge 300 to be simultaneously driven distally along anvil 310 by the distal movement of locking pin 360. Upon reaching anvil shoulder 312 (FIG. 17) distal movement of the cartridge 300 terminates and tissue is clamped between anvil head 320 and cartridge distal end 304. When cartridge distal end 304 abuts shoulder 312, pusher plate aperture 106A and anvil body aperture 314 and locking pin 360 align, permitting the proximal edge of pusher plate aperture 106A to depress locking pin 360 into anvil aperture 314 as discussed below.

In the position shown in FIG. 17, pusher plate aperture 106A aligns with anvil aperture 314. Distal displacement of firing wire 102 slides the proximal edge of pusher plate aperture 106A against locking pin camming surface 362. As the edge of pusher plate aperture 106A slides against the pin camming surface, locking pin 360 is forced downward into aperture 314, compressing spring 370. When locking pin 360 is fully engaged in aperture 314 (FIG. 18) pusher plate aperture 106A has cleared the upper distal edge of locking pin camming surface 362. In this position, pusher plate 104 blocks the upward vertical return of locking pin 360, maintaining the pin in anvil aperture 314. The presence of locking pin 360 in aperture 314 prevents proximal movement of cartridge 300 along anvil 310 during staple firing.

Note that the movement of locking pin 360 into aperture 314 constitutes a dwell period of the surgical stapling apparatus. Handles 18 and 20 continue to be approximated, but staple firing is not commenced. During this dwell period, the user is free to unclamp the tissue for repositioning or selection of an alternative stapling site.

After the pusher plate aperture 106A has cleared the fully engaged locking pin 360, pusher plate fingers 104F engage a staple 330 located in channel 302. Pusher plate 104 drives staple 330 through channel 302 into tissue clamped between cartridge distal end 304 and anvil head 320. The legs of staple 330 are deformed against staple forming cups 322 to fasten the clamped tissue together.

Referring now to FIGS. 19–22 there is illustrated a second embodiment of the staple storage and firing mechanism of the present invention. In this embodiment, an anvil jaw pivotally mounts to a staple cartridge for clamping tissue to be stapled. The staple storage and firing mechanism comprises a housing member 560, FIGS. 20–22 for receiving a staple cartridge 400. Housing arms 562, extending from the proximal end of housing member 560, pivotally mount to the distal ends of endoscopic sections 14a and 14b by pivot pins 700. Pins 700 pass through apertures 564 which are aligned with distal endoscopic section apertures 502, best seen in FIG. 14. By means of this pivotal connection, housing 560 can be articulated with respect to the longitudinal axis of the instrument as previously described.

Housing member 560 receives staple cartridge 400 for holding a plurality of staples 330a. Extending from the proximal end of cartridge 400 are arms 410 having apertures 412 formed therein. Cartridge arms 410 mount the cartridge to housing member 560 through apertures 412 by transverse pin 480. Articulation of housing member 560 thus produces the corresponding orientation of the staple cartridge 400.

Staples 330a are contained within cartridge 400 in adjacent stacked relation. Staple follower 570 urges the staple stack distally through the force of coil spring 572. The distalmost staple is thus positioned for ejection in cartridge staple guide channel 406. Preferably, the staple stack forms an acute angle with the longitudinal axis of the staple cartridge. Angular stacking of the staples facilitates storage of a plurality of staples in a structure configured and dimensioned for endoscopic applications, e.g., for insertion through a 12 mm diameter trocar guide tube.

Pivotally mounted to cartridge 400 by primary pivot pin 450 is anvil jaw 440. At its proximal end anvil jaw arms 442 extend from anvil jaw 440, terminating in angled camming surfaces 444. Camming surfaces 444 permit the anvil jaw to be selectively pivoted by the user between open and closed positions. At its distal end, anvil jaw 440 is configured to cooperate with cartridge 400 to clamp tissue. Staple forming cups 447 in anvil jaw 440, seen in FIGS. 21 and 22, receive staples 330 driven from staple cartridge 400.

Anvil jaw 440 is biased to an open position by spring 490. Spring 490, illustrated in FIGS. 20–22 as a coil compression spring and, alternatively, in FIG. 19 as a leaf spring, connects anvil jaw 440 to cartridge 400. Biasing the anvil jaw open advantageously returns the instrument to a position ready to clamp tissue and fire an additional staple.

Figure 19:
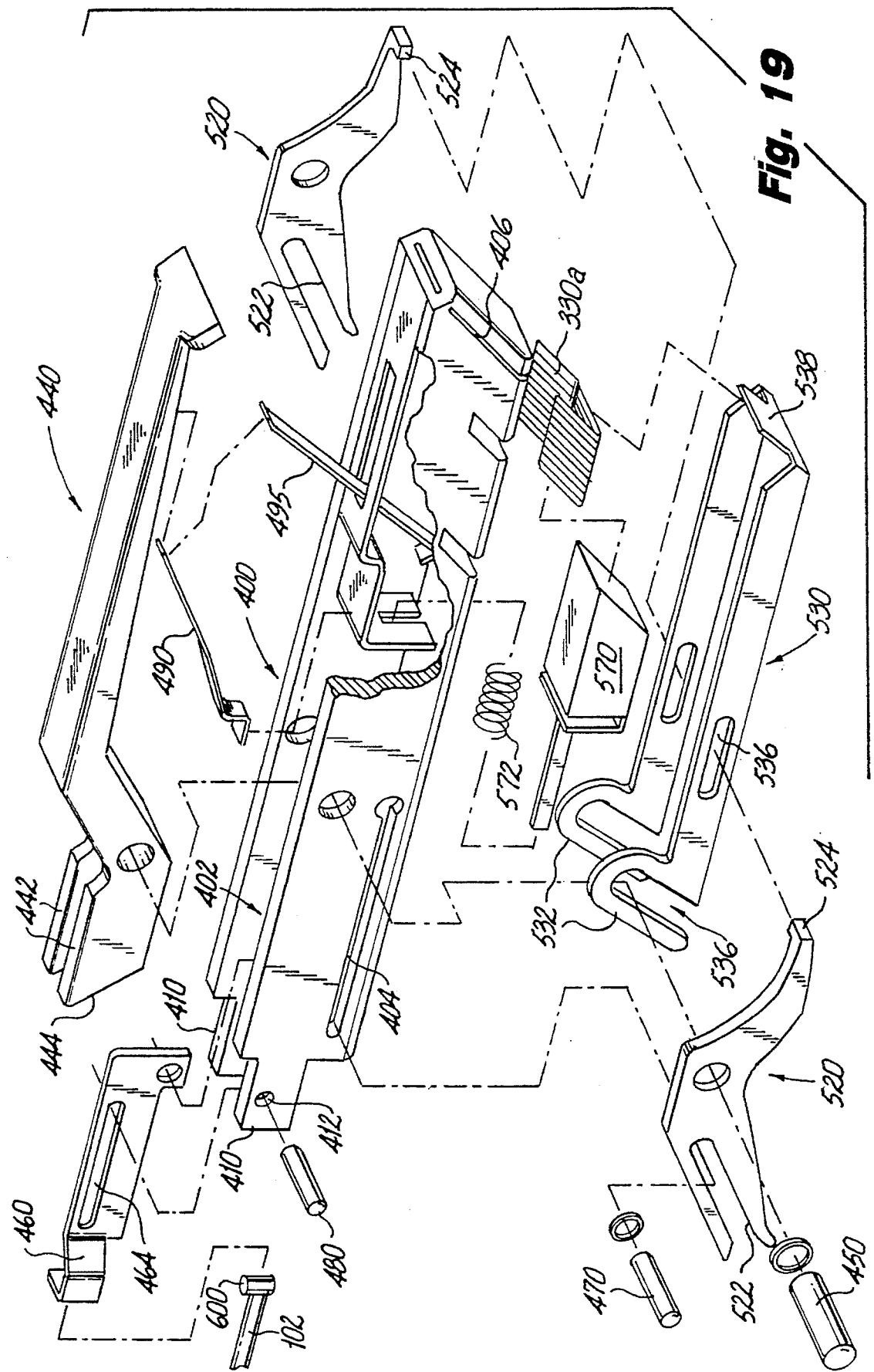

At its proximal end, cartridge 400 is configured to define a central drive channel, 402, best seen in FIG. 19. Central drive channel 402 receives resiliently flexible firing wire 102 for actuating the staple firing mechanism. At its distal end, firing wiring 102 terminates in connecting head 600, illustratively shown as having a T-bar configuration.

Connecting head 600 mounts the driving member for staple firing, pushing link 460. Pushing link 460, adapted for longitudinal reciprocal motion, performs its driving function by means of transverse pivot pin 470 mounted through its distal end. Pin 470 passes through the distal end of pushing link 462 to engage longitudinal cartridge guide slots 404. As pin 470 is driven distally along cartridge guide slots 404 by pushing link 460, it pivots the anvil jaw to a closed position and actuates the staple pusher, described below. Pushing link 460 maintains its longitudinal orientation in the cartridge guide channel through pushing link guide slots 464 cooperating with transverse pin 480.

The staple firing mechanism further includes levers 520 pivotal about primary pivot pin 450. Pivot levers 520 translate the longitudinal reciprocal movement of pushing link 460 into pivotal movement to drive staple pusher 530. At their proximal ends, pivot levers 520 include angled camming slots 522 for receiving pin 470. Pivot lever fingers 524 project inwardly at the distal end of the pivot levers, engaging staple pusher 530 through slots 536. As pushing link 460 drives pin 470 into camming slots 522, the pivot levers are actuated, with fingers 524 sliding proximally in slots 536 to push staple pusher 530 toward anvil jaw 440.

Staple pusher 530 comprises pusher finger 538 at its distal end. Upon actuation by pivot levers 520, pusher finger 538 ejects an individual staple 330a through cartridge staple guide channel 406. At its proximal end, a pair of pusher arms 532 extend from staple pusher 530. Pusher arms 532 terminate in angled camming slots 536 adapted to cooperate with primary pivot pin 450 during staple firing. To bias staple pusher 530 to its unfired position, spring 495, connected between anvil jaw 440 and staple pusher 530, is provided. Spring 495 also assists in biasing anvil jaw 440 to an open position.

In the operation of the surgical apparatus of FIG. 20, approximation of handles 18 and 20 (FIG. 1) advances firing wire 102 distally. As firing wire 102 advances, pushing link 460 moves distally, its longitudinal orientation maintained by slot 464 cooperating with pin 480. Simultaneously, pin 470 slides against anvil jaw camming surface 444, pivoting anvil jaw 440 from the open position of FIG. 20 to the closed position of FIG. 21. During anvil jaw closure, springs 490 and 495 are compressed. Note that this jaw-closed position is used during insertion of the instrument through the trocar guide tube.

Continued approximation of handles 18 and 20 produces further distal movement of pushing link 460, driving pin 470 into the proximal ends of pivot lever camming slots 522. As pin 470 travels along camming slots 522, pivot levers 520 pivot about primary pivot pin 450. Pivot lever fingers 524 slide proximally in slots 536, driving staple pusher 530.

Pivot lever fingers 524 force staple pusher 530 toward anvil jaw 440 directed by the motion of staple pusher angled camming slots 536 along primary pivot pin 450. Simultaneously, staple pusher finger 538 contacts staple 330 to eject the staple through cartridge staple guide channel 406. The staple legs are driven through clamped tissue held between the cartridge and anvil jaw and deformed against anvil jaw staple forming cups 447.

On the return stroke, springs 490 and 495 bias anvil jaw 440 towards an open position. Spring 495 additionally forces staple pusher 530 away from anvil jaw 440 as pusher camming slots 534 simultaneously slide along pin 450, returning the pusher to the unfired position of FIG. 20.

As staple pusher finger 538 clears cartridge staple guide channel 406, stack pusher 570 urges the staple stack forward. The distalmost staple is thus positioned into the guide channel ready to be fired.

During the staple pusher's return to its unfired position, pivot levers 520 pivot downward. Pivot lever fingers 524 slide distally in staple pusher slots 536 while pin 470 slides proximally out of angled pivot lever camming slots 522.

Anvil jaw 440 returns to the open position of FIG. 20 as camming surfaces 444 slide distally along pin 470. Pushing link 460 returns to its original proximal position with pin 470 seated at the proximalmost end of cartridge guide slots 404.

Figure 23:
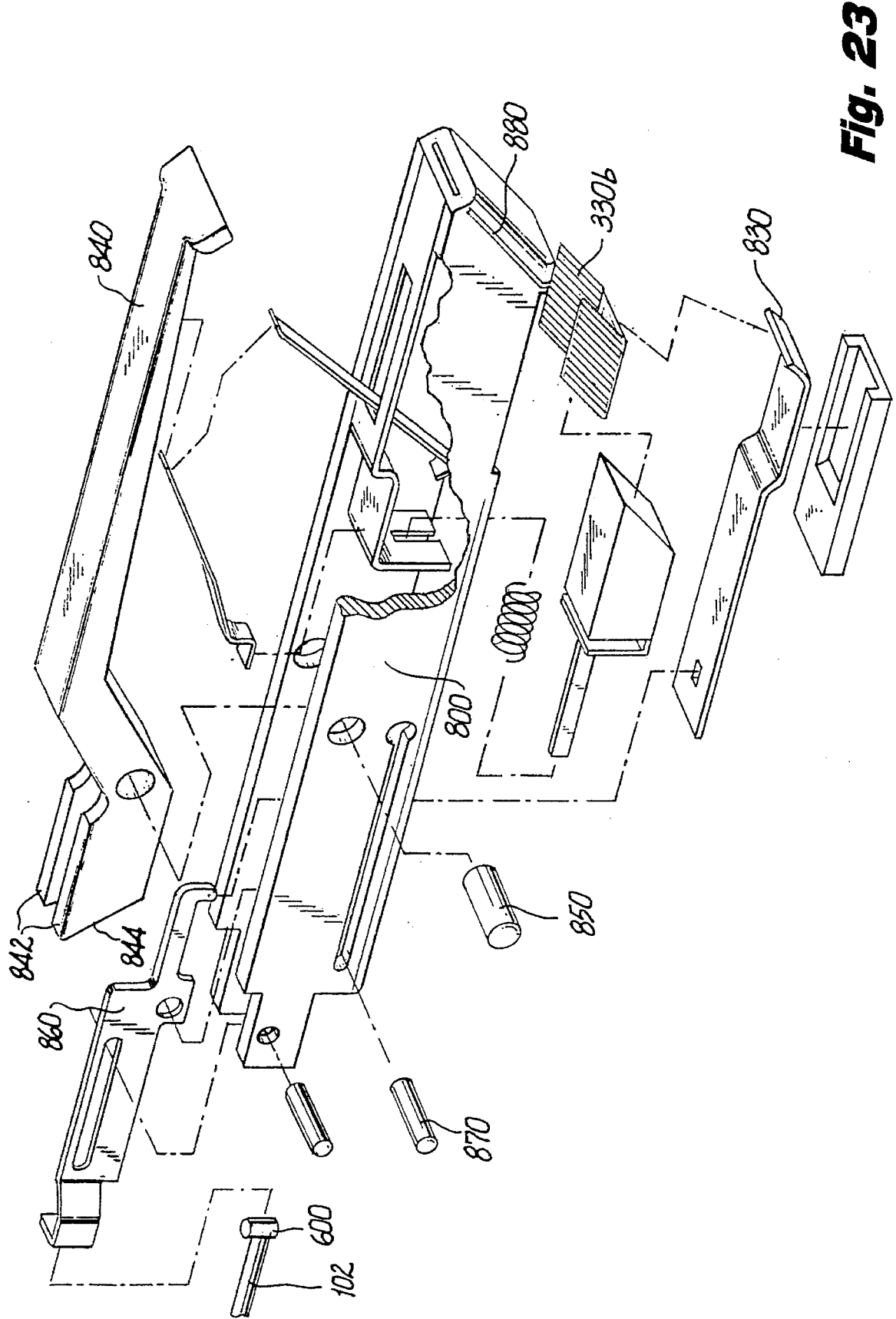
FIG. 23 is an exploded perspective view with parts separated of a staple storage and firing mechanism of a third embodiment of the present invention.
Figure 24:
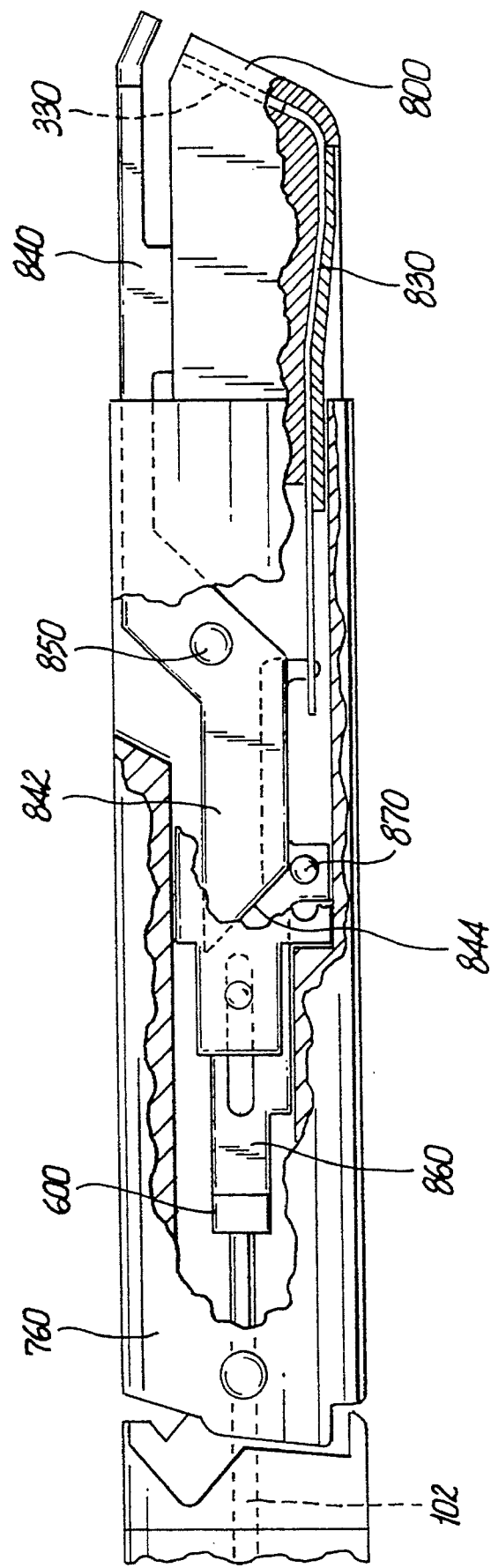
FIG. 24 is a side view in partial cross section showing the staple storage and firing mechanism of FIG. 23 with the anvil jaw in a closed position.
Figure 25:
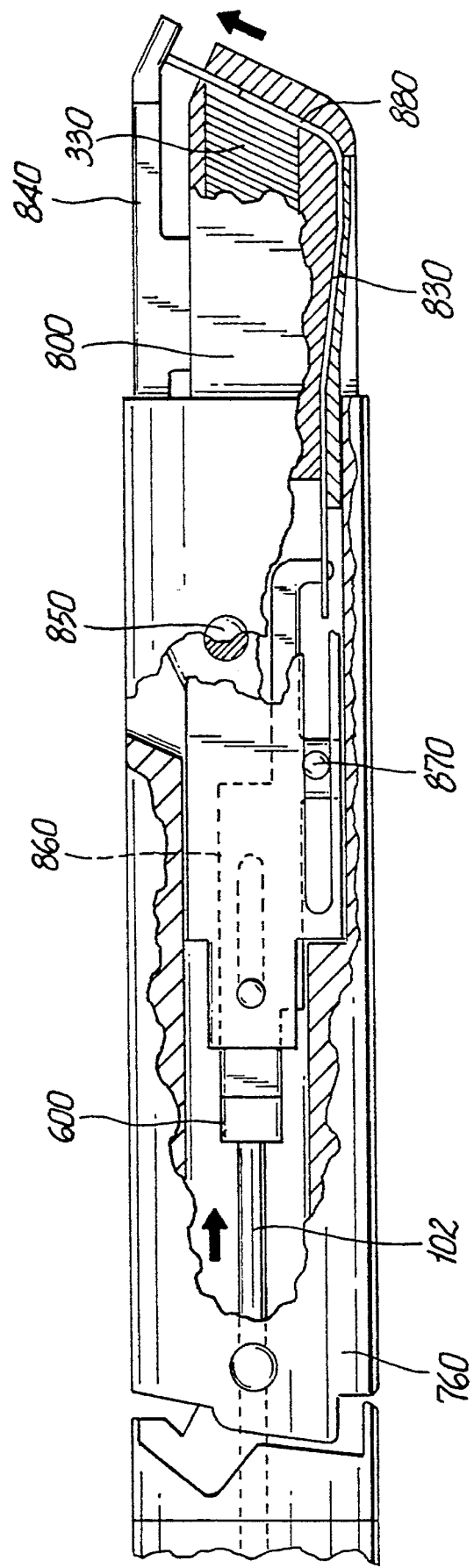
FIG. 25 is a side view in partial cross-section of the staple storage and firing mechanism of FIG. 23 in the process of firing a staple.

A third embodiment of the instrument of the present invention is shown in FIGS. 23–25. As in the previous embodiment, an anvil jaw pivotally mounts to a staple cartridge for clamping tissue to be stapled. The staple storage and firing mechanism comprises a housing member 760 for receiving a staple cartridge 800. Housing member 760 is pivotally connected to the distal end of the endoscopic section, as in the previous embodiment.

Pivotally mounted to cartridge 800 by primary pivot pin 850 is anvil jaw 840. At its proximal, end anvil jaw arms 842 extend from anvil jaw 840, terminating in angled camming surfaces 844. Camming surfaces 844 permit the anvil jaw to be selectively pivoted by the user from an open to a closed position, as in the previous embodiment.

Firing wire 102 terminates in connecting head 600 for mounting the driving member for staple firing, pushing link 860. Pushing link 860 drives staple pusher 830 which is fixedly engaged in the distal end of the pushing link. Staple pusher 830 is fabricated from a shape memory alloy such as NITINOL brand metal alloy. The use of a shape memory alloy for staple pusher 830 allows the staple pusher to be easily deformed as it passes through staple pusher guide channel 880, eliminating the need for a pivotal element to drive the staple pusher, as in the previous embodiment.

In addition to driving the staple pusher, pushing link 860 closes anvil jaw 840 through pin 870. As the pushing link is advanced, pin 870 travels along camming surfaces 844 to move the anvil jaw from an open to a closed position.

The operation of the instrument of FIGS. 23–25 is substantially similar to the operation of the instrument of FIGS. 19–22.

The instrument of the present invention has particular application to vascular tissue, although it can be used to attach or close openings in other types of body tissue. The clamping and closing of individual vessels to effect hemostasis by the stapling apparatus of the present invention saves the surgeon valuable time. The stapling apparatus of the present invention can also be used to attach approximated vessels or vessel portions by inserting each leg of the staple through one of the approximated vessels or vessel portions. The B-shaped formation of the staple legs provides advantageous attachment of the approximated vessels.

The apparatus and staples can be provided in any size matched to meet the needs of a contemplated surgical procedure. The staples are construed from a biocompatible, preferably metallic, material such as titanium or stainless steel.

To use the surgical stapling apparatus of the present invention in laparoscopic and endoscopic procedures, an opening is created in the patient's body. The opening is formed and maintained through a trocar and cannula assembly. The cannula is positioned within the opening in the body and the endoscopic section of the stapling apparatus is inserted into the cannula. Provision is made between the cannula and the endoscopic section to seal the connection therebetween. An exemplary cannula assembly including seal means is disclosed in commonly assigned U.S. Pat. No. 4,943,290 issued Jul. 24, 1990, which is incorporated herein by reference. Also, as shown in FIG. 26, a gaseous seal 250 is provided to seal the actual apparatus from leakage of fluids or insufflating gaseous media. Typically, seal 250 is located within the endoscopic section 14 between collar 60 and the handle portion.

A typical endoscopic section may be approximately 12 mm in diameter with a staple cartridge capable of holding approximately 10 staples of appropriate size. When the endoscopic stapling apparatus is adapted for use with a removable staple cartridge, the spent cartridge can be removed and replaced by a loaded cartridge containing the same or different sized staples. The length of the endoscopic section is typically 14 to 15 inches. An endoscopic section in the embodiment shown will be about 14 inches. However, if pivotal movement of the staple storage cartridge is to be provided between plus 45 degrees and minus 45 degrees solely by distal and proximal movement of collar 22, the endoscopic section will be greater in length, e.g., about 15 inches. The trocar and cannula assembly will be of matching size, i.e., 12 mm, to accommodate the endoscopic section and to prevent unintended ingress or egress of gases therethrough.

While the invention has been particularly shown an described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. Apparatus for remote application of a surgical staple to body tissue comprising:

a frame;

one handle mounted for movement between open and closed positions and connected to said frame;

a generally elongated member connected to said frame and extending distally therefrom;

a support member positioned adjacent a distal end of said elongated member and mounted for pivotal movement with respect thereto, said support member having a cartridge coupled thereto for storing at least one surgical staple;

an anvil operatively coupled to said support member and said cartridge for forming the surgical staple;

means operatively associated with said one handle and extending through said elongated member for moving said cartridge relative to said anvil in response to movement of said one handle from said open position to an intermediate position spaced from said closed position to clamp body tissue between said cartridge and said anvil prior to forming a staple;

a staple firing mechanism operatively connected to said one handle and actuated in response to movement of said one handle from said intermediate position to said closed position and configured to individually advance a surgical staple from said cartridge into said body tissue and against said anvil to form the staple.

2. Apparatus according to claim 1 wherein said anvil includes an anvil head portion located at a distal end thereof and an anvil body portion, said cartridge being slidably mounted to said anvil body portion such that said cartridge longitudinally slides along said anvil body portion in response to movement of said one handle to provide relative motion between said cartridge and said anvil.

3. Apparatus according to claim 2 further comprising means for preventing proximal movement of said cartridge during staple firing comprising:
   a locking pin engaged in an aperture formed within said cartridge; and
   an aperture formed in said anvil body portion for receiving said locking pin.

4. Apparatus according to claim 3 wherein said staple firing mechanism comprises a pushing member adapted at its distal end to engage a staple.

5. Apparatus according to claim 4 wherein said pushing member further comprises an aperture for engaging said locking pin wherein said pushing member aperture and said anvil body aperture align when said cartridge abuts said anvil shoulder.

6. Apparatus according to claim 5 wherein said pushing member aperture engages said locking pin to drive said locking pin into said anvil body aperture.

7. Apparatus according to claim 1 wherein said support member and said anvil are pivotably mounted to said elongated member and are selectively pivotal into a plane outside a longitudinal plane formed by the elongated member of the apparatus such that said cartridge is pivoted therewith.

8. Apparatus according to claim 7 further comprising a control mechanism operatively associated with a proximal end portion of said elongated member and configured to pivot said support means and said anvil.

9. Apparatus according to claim 1 wherein said anvil is pivotally connected to said cartridge.

10. Apparatus according to claim 9 further comprising a first camming mechanism linked to said one handle for pivoting said anvil.

11. Apparatus according to claim 10 further comprising a second camming mechanism linked to said one handle to actuate said staple firing mechanism.

12. Apparatus according to claim 10 wherein said first camming mechanism comprises:
    an elongated firing rod linked to said at least one handle and adapted for longitudinal reciprocal motion in response to movement of said one handle;
    a driving pin cooperating with the distal end of said firing rod and movable therewith; and
    a camming surface on a proximal end portion of said anvil whereby travel of said driving pin against said camming surface pivots said anvil between open and closed positions.

13. Apparatus according to claim 12 wherein said staple firing mechanism includes a staple pusher configured at its distal end to engage an individual staple and including a camming slot at its proximal end.

14. Apparatus according to claim 13 further comprising a linking member pivotally connected to said cartridge and having a camming slot at its proximal end for receiving said driving pin and having a projection at its distal end for engaging said staple pusher whereby travel of said driving pin in said camming slot pivots said linking member to actuate said staple pusher.

15. Apparatus according to claim 12 wherein said staple firing mechanism includes a staple pusher fabricated from a shape memory material adapted at its distal end to engage an individual staple and linked at its proximal end to said elongated firing rod.

16. Apparatus according to claim 1 wherein said elongated member is rotatable about a longitudinal axis.

17. Apparatus according to claim 1 wherein said cartridge is removably mounted to said support member.

18. Apparatus according to claim 1 further comprising means operatively connected to said staple firing mechanism for preventing incomplete staple firing.

19. Apparatus according to claim 18 wherein said means for preventing incomplete staple firing comprises a ratchet mounted to said frame and adapted to engage a pawl mounted to staple firing mechanism wherein said ratchet engages said pawl during staple firing.

20. Apparatus for endoscopic application of a surgical staple to body tissue comprising:
    a frame member;
    a trigger member pivotally connected to said frame member;
    a generally elongated endoscopic housing member connected to said frame member and extending distally therefrom;
    a cartridge pivotable with respect to the distal end of said endoscopic housing member and adapted to hold at least one surgical staple;
    an anvil operatively associated with the housing member and positioned adjacent the cartridge for forming an individual surgical staple;
    means for providing relative motion between said cartridge and said anvil to clamp body tissue between said cartridge and said anvil;
    a staple firing mechanism cooperating with said trigger for individually advancing said surgical staple into said body tissue and against said anvil;
    means connected to said staple firing mechanism for preventing incomplete staple firing;
    a rotation control member operatively associated with a proximal portion of the endoscopic housing member for rotating said endoscopic housing member about a longitudinal axis extending therethrough; and
    a gaseous seal positioned within said endoscopic member.

21. Apparatus according to claim 20 wherein said anvil comprises an anvil head portion and an anvil body portion, said cartridge being slidably mounted to said anvil body portion such that said cartridge slides along said anvil body portion to provide said relative motion between said cartridge and said anvil.

22. Apparatus according to claim 21 further comprising means to prevent proximal movement of said cartridge during staple firing comprising:
    a locking pin located within said cartridge and having an angled camming surface; and
    an aperture formed in said anvil body portion for receiving said locking pin.

23. Apparatus according to claim 22 wherein said staple firing mechanism further comprises a pushing member having an aperture for engaging said angled camming surface of said locking pin such that said pushing member aperture engages said locking pin camming surface to drive said locking pin into said anvil body aperture.

24. Apparatus according to claim 20 wherein said anvil is pivotally connected to said cartridge.

25. Apparatus according to claim 24 further comprising a camming mechanism operatively associated with said anvil and configured to pivot said anvil and to actuate said staple firing mechanism.

26. Apparatus according to claim 25 wherein said camming mechanism comprises a camming surface on a proximal end portion of said anvil whereby travel of said driving pin against said camming surface pivots said anvil between open and closed positions.

27. Apparatus according to claim 24 wherein said staple firing mechanism includes a linking member mounted for longitudinal reciprocal motion and having a driving pin passing through its distal end.

28. Apparatus according to claim 27 wherein said staple firing mechanism further comprises a staple pusher fabricated from shape memory material connected to said linking member.

29. Apparatus for endoscopic application of a surgical staple to body tissue comprising:

a frame;

a trigger member pivotally connected to said frame means;

a generally elongated endoscopic housing member connected to said frame and extending distally therefrom;

a cartridge cooperating with said endoscopic housing member for storing at least one surgical staple;

an anvil operatively associated with said cartridge and positioned adjacent thereto for closing a surgical staple;

a staple firing mechanism including a staple pusher cooperating with said trigger member which when actuated individually advances said surgical staple into said body tissue and against said anvil;

means for providing relative motion between said cartridge and said anvil and for actuating said staple firing mechanism wherein in a first movement of said trigger member said cartridge moves relative to said anvil to a clamped position in which tissue is clamped between said cartridge and said anvil, and in a second subsequent movement of said trigger member said staple pusher is actuated; and a spring biased locking pin disposed within said cartridge and configured to maintain said cartridge and said anvil in said clamped position during said second movement of said trigger member.

30. Apparatus according to claim 29 wherein said locking pin disposed within said cartridge has an angled camming surface provided thereon and an aperture is formed in said anvil for receiving said locking pin.

31. Apparatus according to claim 30 wherein said staple pusher includes an aperture for engaging said angled camming surface of said locking pin.

32. Apparatus according to claim 31 wherein said aperture in said staple pusher engages said camming surface to drive said locking pin into said aperture in said anvil.

33. Apparatus as recited in claim 32 wherein said locking pin provides an indication that said first movement of said trigger member has been terminated by providing a second movement dwell period.

34. Apparatus according to claim 33 wherein said second movement dwell comprises the driving of said locking pin into said anvil body aperture.

35. Apparatus according to claim 34 further comprising means to prevent incomplete staple firing during said subsequent movement of said trigger member.

* * * * *